US008226236B2

(12) United States Patent
Williams et al.

(10) Patent No.: US 8,226,236 B2
(45) Date of Patent: Jul. 24, 2012

(54) METHOD AND APPARATUS FOR IMAGING IN AN EYE

(75) Inventors: David Williams, Fairport, NY (US); Jessica Wolfing Morgan, Glassboro, NJ (US); Daniel Gray, Fife (GB); Alfredo Dubra, Rochester, NY (US)

(73) Assignee: University of Rochester, Rochester, NY (US)

( * ) Notice: Subject to any disclaimer, the term of this patent is extended or adjusted under 35 U.S.C. 154(b) by 1236 days.

(21) Appl. No.: 11/798,902

(22) Filed: May 17, 2007

(65) Prior Publication Data

US 2008/0007693 A1 Jan. 10, 2008

Related U.S. Application Data

(60) Provisional application No. 60/801,059, filed on May 18, 2006.

(51) Int. Cl.
*A61B 3/10* (2006.01)
(52) U.S. Cl. .................................... 351/221; 351/200
(58) Field of Classification Search .................. 351/221
See application file for complete search history.

(56) References Cited

U.S. PATENT DOCUMENTS

| | | | |
|---|---|---|---|
| 7,648,242 B2 * | 1/2010 | Ferguson et al. | 351/221 |
| 2003/0218672 A1 * | 11/2003 | Zhang et al. | 348/14.16 |
| 2003/0223037 A1 * | 12/2003 | Chernyak | 351/209 |
| 2006/0072018 A1 * | 4/2006 | Inaba et al. | 348/208.99 |

OTHER PUBLICATIONS

Drexler, W. et al. "Ultrahigh-resolution ophthalmic optical coherence tomography," Nat. Med 7, 502-507 (2001).
Leitgeb, R. et al. "Ultrahigh resolution Fourier domain optical coherence tomography," Opt. Express 12, 2156-2165 (2004).
Cense, B. et al. "Ultrahigh-resolution high-speed retinal imaging using spectral-domain optical coherence tomography," Opt. Express 12, 2435-2447 (2004).
Wojtkowski, M. et al. "Ultrahigh-resolution, high-speed, Fourier domain optical coherence tomography and methods for dispersion compensation," Opt. Express 12, 2404-2422 (2004).
Artal, P. et al. "High-resolution imaging of the living human fovea: measurement of the intercenter cone distance by speckle interferometry," Opt. Lett. 14, 1098-1100 (1989).
Miller, D. T. et al. "Images of Cone Photoreceptors in the Living Human Eye," Invest. Ophthalmol. Visual Sci. 36, S188-S188 (1995).
Liang, J. et al. "Aberrations and retinal image quality of the normal human eye," J. Opt. Soc. Am. A 14, 2873-2883 (1997).
Liang, J. et al. "Supernormal vision and high-resolution retinal imaging through adaptive optics," J. Opt. Soc. Am. A 14, 2884-2892 (1997).
Vargas-Martin, F. et al. "Correction of the aberrations in the human eye with a liquid-crystal spatial light modulator: limits to performance," J. Opt. Soc. Am. A 15, 2552-2562 (1998).
Roorda, A. et al. "The arrangement of the three cone classes in the living human eye," Nature 397, 520-522 (1999).

(Continued)

*Primary Examiner* — James Jones
(74) *Attorney, Agent, or Firm* — William Greener; Bond, Schoeneck & King, PLLC

(57) ABSTRACT

A method for in vivo imaging of at least one cell including: first obtaining a first image of at least one cell; second obtaining a second image of the at least one cell; adjusting at least one of the first image and the second image to account for a movement of the at least one cell; generating a final image based at least in part on the adjusting.

20 Claims, 30 Drawing Sheets

OTHER PUBLICATIONS

Yoon, G. et al. "Dynamic correction of the eye's aberration with the Rochester 2nd generation adaptive optics system.," Invest. Ophthalmol. Visual Sci. 42, S99-S99 (2001).
Hofer, H. et al. "Improvement in retinal image quality with dynamic correction of the eye's aberrations," Optical Society of America, Optics Express vol. 8, No. 11, 631-643 (2001).
Roorda, A. et al. "Packing arrangement of the three cone classes in primate retina," Vision Res. 41, 1291-1306 (2001).
Roorda, A. et al. "Optical fiber properties of individual human cones," J. Vis. 2, 404-412 (2002).
Roorda, A. et al. "Adaptive optics scanning laser ophthalmoscopy," Opt. Express 10, 405-412 (2002).
Pallikaris, D. et al. "The Reflectance of Single Cones in the Living Human Eye," Invest. Opthalmol. Vis. Sci. 44, 4580-4592 (2003).
Carroll, J. et al. "Functional photoreceptor loss revealed with adaptive optics: An alternate cause of color blindness," Proc. Natl. Acad. Sci. U.S.A. 101, 8461-8466 (2004).
Glanc, M. et al. "Towards wide-field retinal imaging with adaptive optics," Opt. Commun. 230, 225-238 (2004).
Putnam, N. M. et al. "The locus of fixation and the foveal cone mosaic," J. Vis. 5, 632-639 (2005).
Jiang, W. et al. "Medical and Industrial Application of Adaptive Optics in Institute of Optics and Electronics, Chinese Academy of Sciences," in 5th International Workshop on Adaptive Optics for Industry and Medicine, Proc. of SPIE vol. 6018, 601801-1-601801-16 (2005).
Hofer, H. et al. "Organization of the human trichromatic cone mosaic," Journal of Neuroscience, Oct. 19, 2005 25(42):9669-9679. "Erratum," Journal of Neuroscience, Jan. 11, 2006 26(2):722.
Merino, D. et al. "Adaptive optics enhanced simultaneous en-face optical coherence tomography and scanning laser ophthalmoscopy," Opt. Express 14, 3345-3353 (2006).
Wolfing, J. I. et al. "High-resolution retinal imaging of cone-rod dystrophy," Ophthalmology 113, 1014-1019 (2006).
Bindevvald, A. et al. "Visualization of retinal pigment epithelial cells in vivo using digital high-resolution confocal scanning laser ophthalmoscopy," Am. J. Opthalmol. 137, 556-558 (2004).
Cordeiro, M. F. et al. "Real-time imaging of single nerve cell apoptosis in retinal neurodegeneration," Proc. Natl. Acad. Sci. U.S.A. 101, 13352-13356 (2004).
Imanishi, Y. et al. "Noninvasive two-photon imaging reveals retinyl ester storage structures in the eye," J. Cell. Biol. 164, 373-383 (2004).
Hermann, B. et al. "Adaptive-optics ultrahigh-resolution optical coherence tomography," Opt. Lett. 29, 2142-2144 (2004).
Zhang, Y. et al. "Adaptive optics parallel spectral domain optical coherence tomography for imaging the living retina," Opt. Express 13, 4792-4811 (2005).
Fernandez, E. J. et al. "Three-dimensional adaptive optics ultrahigh-resolution optical coherence tomography using a liquid crystal spatial light modulator," Vision Res. 45, 3432-3444 (2005).
Zawadzki, R. J. et al. "Adaptive-optics optical coherence tomography for high-resolution and high-speed 3D retinal in vivo imaging," Opt. Express 13, 8532-8546 (2005).
Patterson, B. A. Personal Communication and "General Purpose Control System for Scanning Laser Ophthalmoloscopes". Nov. 26, 2002.
Dacey, D. M. et al. "Fireworks in the primate retina: In vitro photodynamics reveals diverse LGN-projecting ganglion cell types," Neuron 37, 15-27 (2003).
Strauss, O. et al. "The retinal pigment epithelium in visual function," Physiol. Rev. 85, 845-881 (2005).
Feeney-Burns, L. et al. "Aging Human RPE—Morphometric Analysis of Macular, Equatorial, and Peripheral Cells," Invest. Ophthl. Vis. Sci. 25, 195-200 (1984).
Zinn, K. M. et al. "Anatomy of the human retinal pigment epithelium", in *The Retinal Pigment Epithelium*, K. M. Zinn and M. F. Marmor (Harvard University Press, Cambridge, 1979), pp. 3-21.
Snodderly, D. M. et al. "Retinal pigment epithelial cell distribution in central retina of rhesus monkeys," Invest. Ophthalmol. Visual Sci. 43, 2815-2818 (2002).
Curcio, C. A. et al. "Human Photoreceptor Topography," J. Comp. Neurol. 292, 497-523 (1990).
Delori, F. C. "Spectrophotometer for noninvasive measurement of intrinsic fluorescence and reflectance of the ocular fundus," Appl. Opt. 33, 7439-7452 (1994).

Delori, F. C. et al. "In vivo fluorescence of the ocular fundus exhibits retinal pigment epithelium lipofuscin characteristics," Invest. Ophthalmol. Visual Sci. 36, 718-729 (1995).
Von Ruckmann, A. et al. "Distribution of fundus autofluorescence with a scanning laser ophthalmoscope," British Journal of Ophthalmology. 79, 407-412 (1995).
Von Ruckmann, A. et al. "Abnormalities of fundus autofluorescence in central serous retinopathy," American Journal of Ophthalmology, vol. 133, No. 6, 780-786 (Jun. 2002).
Holz, F. G. et al. "Fundus autofluorescence and development of geographic atrophy in age-related macular degeneration," Invest. Ophthalmology. Visual Sci. 42, 1051-1056 (2001).
Delori, F. C. et al. "Age-related accumulation and spatial distribution of lipofuscin in RPE of normal subjects," Invest. Ophthalmology. Visual Sci. 42, 1855-1866 (2001).
Lois, N. et al. "Fundus autofluorescence in Stargardt macular dystrophy-fundus flavimaculatus," Am. J. Ophthalmology. 138, 55-63 (2004).
Reinholz, F. et al. "Simultaneous three wavelength imaging with a scanning laser ophthalmoscope," Cytometry 37, 165-170 (1999).
ANSI, *American National Standard for the Safe Use of Lasers ANSI Z136.1-2000*, (Laser Institute of America, Orlando, FL 2000).
Hofer, H. et al. "Dynamics of the eye's wave aberration," J. Opt. Soc. Am. A 18, 497-506 (2001).
Cushion, J. et al. "General purpose control system for scanning laser ophthalmoscopes," Clin Experiment Ophthalmology 31, 241-245 (2003).
Bischoff, P. M. et al. "Simultaneous Indocyanine Green and Fluorescein Angiography," Retina 15, 91-99 (1995).
Fuchs, A. F. et al., "A method for measuring horizontal and vertical eye movement chronically in the monkey," J. Appl. Physiol. 21, 1068-1070 (1966).
Coletta, N. J. et al. "Psychophysical Estimate of Parafoveal Cone Spacing," J. Opt. Soc. Am. A, Optical Society of America. vol. 4, No. 8, 1503-1513 (1987).
Wyszecki, G. et al. *Color Science: Concepts and Methods, Quantitative Data and Formulas* (John Wiley & Sons, Inc., New York, 1967), Chap. 2.
Burke, J. M. et al. "Mosaicism of the retinal pigment epithelium: seeing the small picture," Mol. Interv. 5, 241-249 (2005).
Packer, O. et al. "Photoreceptor Topography of the Retina in the Adult Pigtail Macaque (Macaca-Nemestrina)," J. Comp. Neurol. 288, 165-183 (1989).
Weinhaus, R. S. et al. "Comparison of Fluorescein Angiography with Microvascular Anatomy of Macaque Retinas," Exp. Eye Res. 61, 1-16 (1995).
Lois, N. et al. "Quantitative evaluation of fundus autofluorescence imaged "in vivo" in eyes with retinal disease," Br. J. Ophthalmol. 84, 741-745 (2000).
Morgan, J. W. et al. "Dual-wavelength focusing and simultaneous image registration for in vivo high-resolution retinal imaging," OSA Annual Vision Meeting, Oct. 9, 2006.
Morgan, J. W. et al. "Imaging Individual Human Retinal Pigment Epithelial Cells In Vivo".
Fernandez, E. J. et al. "Ocular aberrations as a function of wavelength in the near infrared measured with a femtosecond laser". Optics Express, vol. 13, No. 2, Jan. 24, 2005, pp. 400-409.
Thibos, L. N. et al. "The chromatic eye: a new reduced-eye model of ocular chromatic aberration in humans". Applied Optics, vol. 31, pp. 3594-3600 (1992).
Baraas et al., "Adaptive Optics Retinal Imaging Reveals S-Cone Dystrophy in Tritan Color-Vision Deficiency". 24 JOSA A, pp. 1438-1447 (2007).
Hammer, D. X. et al. "Adaptive optics scanning laser ophthalmoscope for stabilized retinal imaging," Opt. Express 14, 3354-3367 (2006).
Hammer, D. et al, "Image Stabilization for Scanning Laser Opthalmoscopy," Opt. Express vol. 10 No. 26, 1542-1549 (2002).
Hammer, D. et al, "Compact Scanning Laser Ophthalmoscope with High Speed Retinal Tracker," Applied Opt. vol. 42 No. 22, 4621-4632 (2003).
Ferguson, D. et al, "Tracking Optical Coherence Tomography," Opt. Letters, vol. 29 No. 18, 2139-2141, (2004).

\* cited by examiner

REFLECTANCE IMAGING OF THE PHOTORECEPTOR LAYER

FLUORESCENCE IMAGING OF THE RPE

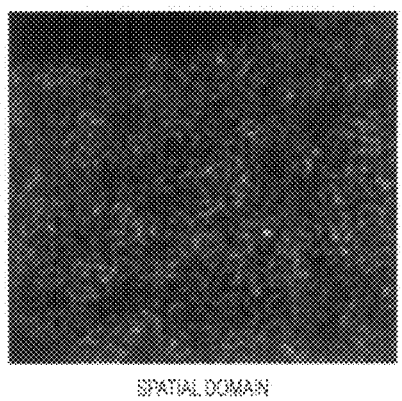 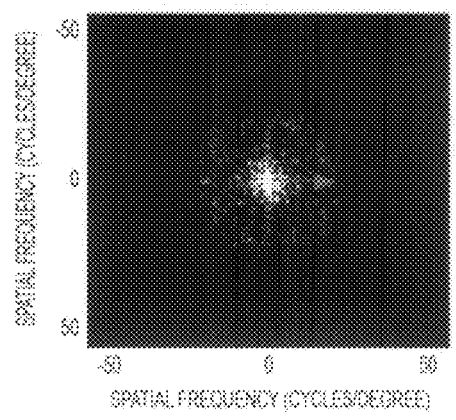
FIGURE 14(a)
FIGURE 14(b)

|  | 10 DEGREES SUPERIOR | 13.75 DEGREES SUPERIOR | 15 DEGREES SUPERIOR |
|---|---|---|---|
| RPE SPATIAL FREQUENCY (CYCLES/DEGREE) | 21.25 | 21.25 | 19.5 |
| RPE CELL SPACING ($\mu m$) | 13.13 | 13.13 | 14.31 |
| RPE DENSITY (RPE CELLS/$mm^2$) | 5,200 | 5,400 | 4,700 |
| CONE DENSITY (CONES/$mm^2$)** | 8,500 | 6,700 | 5,800 |

FIGURE 14(c)

METHOD AND APPARATUS FOR IMAGING IN AN EYE

CLAIM TO PRIORITY

This application claims priority to U.S. Provisional Patent Application Ser. No. 60/801,059, filed May 18, 2006, the entire contents of which are hereby incorporated by reference.

CROSS-REFERENCE TO RELATED APPLICATIONS

The present invention may be related to the inventions described and claimed in U.S. Pat. No. 5,777,719; U.S. Pat. No. 5,949,521; U.S. Pat. No. 6,095,651; U.S. patent application Ser. No. 10/529,067, filed Dec. 23, 1997 and entitled Apparatus for Improving Vision and Retinal Images; U.S. Pat. No. 6,338,559; U.S. Pat. No. 6,379,005; and U.S. Pat. No. 6,890,076, the contents of each of which are herein incorporated by reference.

FEDERALLY SPONSORED RESEARCH

The invention described in this application was supported by NIH Grant BRP-EY014375; NIH Training Grant EY07125; NIH Core Grant EY001319; NSF Grant CFAO-AST-9876783; and NIH Grant EY014375.

BACKGROUND OF THE INVENTION

The present invention relates generally to devices and methods for optical imaging related to the diagnosis and treatment of retinal disease. In particular, the present invention relates to the field of noninvasive investigation of retinal cells such as ganglion cells and retinal pigment epithelial (RPE) cells.

In the past, it was difficult to image certain types of cells in the area of the retina, unless the cells had been excised from the subject's body. In light of these difficulties, the inventors of the present invention developed methods and devices to noninvasively investigate retinal cells, such as retinal ganglion cells and RPE cells.

SUMMARY OF THE INVENTION

A first non-limiting aspect of the invention provides a method for in vivo imaging of at least one cell, which includes: first obtaining a first image of at least one cell; second obtaining a second image of the at least one cell; adjusting at least one of the first image and the second image to account for a movement of the at least one cell; and generating a final image based at least in part on the adjusting.

Another aspect of the invention provides an adaptive optics scanning laser opthalmoscope (AOSLO), which includes: at least one light source adapted for at least one of fluorescence and reflectance excitation; at least one beam splitter; at least one element adapted for wavefront correction; at least one vertical scanner; at least one horizontal scanner adapted to generate a synchronization signal for use by the at least one vertical scanner; at least one band pass fluorescence filter; at least one detector; and scanner control electronics adapted to adjust at least one of the at least one horizontal scanner and the at least one vertical scanner.

Yet another aspect of the invention provides a method for in vivo imaging of at least one cell, the method including: obtaining a reflectance image of at least one cell; obtaining a fluorescence image of the at least one cell; adjusting at least one of the reflectance image and the fluorescence image to account for a movement of the at least one cell; and generating a final image based at least in part on the adjusting.

Another aspect of the present invention provides a method for in vivo imaging of at least one macroscopic feature, the method including: first obtaining a first image of at least one macroscopic feature; second obtaining a second image of the at least one macroscopic feature; adjusting at least one of the first image and the second image to account for a movement of the at least one macroscopic feature; and generating a final image based at least in part on the adjusting.

Still another aspect of the invention provides a method for in vivo monitoring disease, the method including: first obtaining a first image of at least one feature; second obtaining a second image of the at least one feature; adjusting at least one of the first image and the second image to account for a movement of the at least one feature; generating a final image based at least in part on the adjusting; and determining a status of at least one disease based at least in part on the final image.

BRIEF DESCRIPTION OF THE DRAWINGS

This patent or application file contains at least one drawing executed in color. Copies of this patent or patent application publication with color drawing(s) will be provided by the U.S. Patent and Trademark Office upon request and payment of the necessary fee.

A more complete appreciation of the invention and many of the attendant advantages thereof will be readily obtained as the same becomes better understood by reference to the following detailed description when considered in connection with the accompanying drawings, wherein:

FIGS. 14(a) and 14(b) illustrate exemplary images obtained in the spatial domain and the frequency domain;

FIG. 14(c) is a chart illustrating exemplary imaging results;

DETAILED DESCRIPTION OF THE EMBODIMENTS

Figure 1:
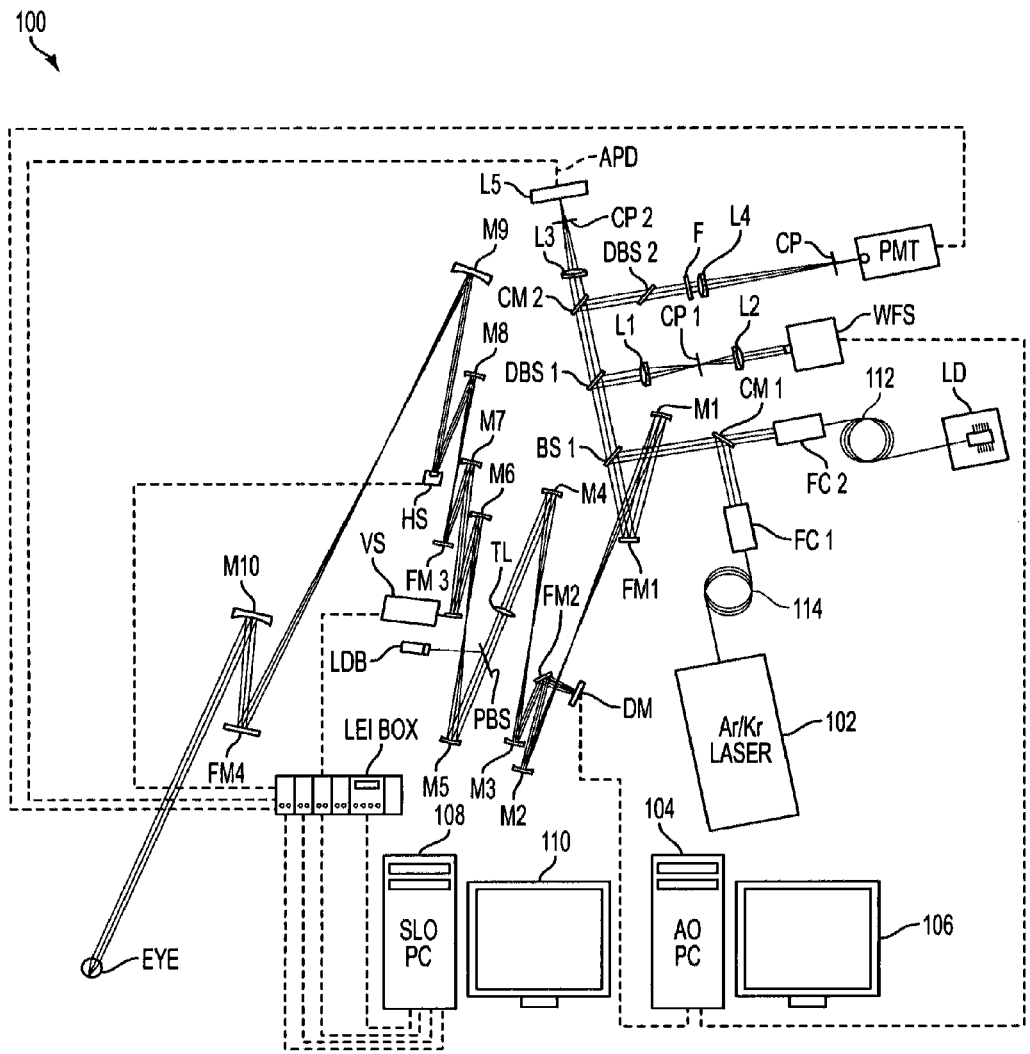
FIG. 1 illustrates an exemplary configuration of an adaptive optics scanning laser opthalmoscope according to a non-limiting aspect of the invention.

Referring now to the drawings, wherein like reference numerals designate the same or corresponding parts throughout the several views, FIG. 1 illustrates a non-limiting example of an adaptive optics scanning laser opthalmoscope (AOSLO) 100. Due to the relatively high magnification and reduced impact of higher order aberrations in the AOSLO shown in FIG. 1, fine structures such as ganglion cell axons can be resolved.

Retinal ganglion cells are of interest because they provide the retinal output signal to the brain, the functional role is unknown for most of the 15-20 morphologically distinct ganglion cell classes, and they are one of the most vulnerable retinal cells to eye disease. Ganglion cell loss is the cause of blindness in glaucoma, the most prevalent cause of irreversible blindness in the United States. However, ganglion cells are difficult to image because their reflectance is roughly 60 times less than that of cones and they are entangled with Müller and amacrine cells of similar refractive index. Fluorescence imaging with the use of dyes or natural fluorophores is a means of providing contrast to transparent retinal cells that has rarely been applied to in vivo high resolution retinal imaging.

RPE cells are responsible for assisting in the regeneration of retinal in the visual cycle, for providing the metabolic support needed by the photoreceptors, and for the phagocytosis of the photoreceptor outer segments. Additionally, RPE cells are affected in retinal diseases including age-related macular degeneration, Stargardt's macular dystrophy, and Best's disease. Despite their important role in the retina, RPE cell morphology across retina eccentricity has not been studied to the same extent as the structure of the photoreceptors. RPE cells are usually not resolved in conventional scanning laser opthalmoscopes, even those that are equipped with adaptive optics. Presumably, the RPE cells are obscured by the waveguiding photoreceptors that lie immediately in front of them in the retina. One of the difficulties of imaging RPE cells in vivo is that autofluorescence images are blurred by eye motion during the long integration times required due to the weak autofluorescence signal. By combining a method involving simultaneous imaging in two spectral bands that allows the integration of very weak signals across many frames despite inter-frame eye movements, the present inventors have succeeded in resolving the mosaic of RPE cells using, for example, lipofuscin autofluorescence.

To image ganglions and RPE cells, the fluorescence AOSLO instrument may use a variety of fluorescence markers, and the markers may be either (or both of) injected or intrinsic. For example, a high resolution fluorescein angiography may enable complete visibility of a connected network of very fine capillaries around the foveal avascular zone. The full width, half maximum of five capillaries may, for example, when measured around the foveal avascular zone, range from 5 to 9 µm. This range may be caused by blurring from uncorrected aberrations or low quality reflectance images which yielded a poor registration. Generally, histological measurements in macaque monkeys have shown a range of 3.2 to 7 µm. The fluorescein signal may be strong enough to detect in a single frame and blood flow may be observed as the dye travels through vessels, such as small capillaries.

The AOSLO 100 of FIG. 1 includes an adjustable scanning system with a variable field of view (e.g., variable 1-3.5 degrees). As shown in FIG. 1, the AOSLO 100 may include an adaptive optics system (including, for example, a Shack-Hartmann wavefront sensor, a MEMS deformable mirror, and a laser beacon), two imaging lasers, and two detectors for simultaneous reflectance and fluorescence imaging. As an alternative to the MEMS deformable mirror, a liquid crystal or other suitable device may be used.

As described above, the AOSLO 100 may include several light sources. For example, the AOSLO 100 may include an 830 nm laser diode LD. The laser diode LD may be useful for cone reflectance imaging. The AOSLO 100 of FIG. 1 may also include a tunable Ar/Kr laser 102 with a wavelength range of approximately 488 nm to approximately 568 nm for fluorescence excitation. A 904 nm laser diode (as a wavefront sensor—WFS) may also be provided.

The AOSLO 100 may include an avalanche photodiode (APD) for 830 nm reflectance imaging. The AOSLO may also include a photomultiplier tube PMT for low light fluorescence detection.

Two computer systems, the scanning laser opthalmoscope (SLO) PC 108 and the adaptive optics (AO) PC 104 may be included in the AOSLO 100. Each of the PCs 104 and 108 may have its own monitor (106, 110). The AO PC 104 may be used to control the AO correction, and the SLO PC 108 may be used to acquire retinal images.

The AOSLO 100 may include lenses L1-L5; spherical mirrors M1-M10; fold mirrors FM1-FM4; cold mirrors CM1-CM2; fiber collimators FC1-FC2; dichroic beam splitters DBS1-DBS2; confocal pinholes CP1-CP2; a laser diode beacon LDB; a 90/10 parallel plate AR coated beam splitter BS1; a MEMS deformable mirror DM; an ophthalmic trial lens TL; a pellicle beam splitter PBS; a vertical scanner (26 Hz) VS; a horizontal scanner (15.1 kHz) HS; a band pass fluorescence filter F; a photomultiplier tube PMT; an avalanche photodiode APD; and scanner control electronics (LEI box). In the AOSLO 100 of FIG. 1, the laser diode LD was a single-mode fiber coupled 830 nm laser diode from Axcel Photonics of Marlborough, Mass. (USA).

The laser diode LD may be used for reflectance imaging of the retina. Generally, near infrared (NIR) wavelengths may be preferred for reflectance imaging, because the ANSI guidelines for the safe use of lasers are more relaxed. Additionally, more light is reflected from the retina in this part of the spectrum. NIR wavelengths are also near the peak quantum efficiency of the silicone APD used to capture the reflectance image.

The Ar/Kr laser 102 shown in FIG. 1 may be an air cooled argon/krypton laser. In this non-limiting example, the Ar/Kr laser 102 was obtained from Melles Griot in Carlsbad, Calif. (USA). The Ar/Kr laser 102 may have multiple lines of different wavelengths. For example, the Ar/Kr laser 102 may have nine lines from 476 nm to 676 nm that provide wavelengths for fluorescence excitation. If desired, the output of the laser may be passed through a variable frequency acousto-optic modulator (AOM), which enables shutter control and light modulation. A suitable AOM may be obtained from Brimrose in Baltimore, Md. (USA).

Light may be modulated pixel-by-pixel using a pattern generator such as a PCI pattern generator, as desired. A suitable PCI pattern generator may be obtained from Spectrum in Grosshansdorf, Germany. The PCI pattern generator may be synchronized to the scanning system. Output light from the light sources may be coupled into a single mode, polarization maintaining optical fiber for delivery to FC1 and FC2. The optical fiber is illustrated by the two coils 112 and 114 in FIG. 1. A cold mirror CM1 permits both sources to enter the system simultaneously and to pass through the same entrance pupil into the system, the image of which may have a diameter of 6.6 mm at the pupil of the eye. Other diameters may be suitable, depending on the desired purpose.

A 90/10 anti-reflection (AR) coated parallel plate beam splitter BS1, which may be oriented at 45 degrees, is adapted to reflect imaging light into the system and to transmit light for wavefront sensing and retinal imaging. A 904 nm, 30 mW laser diode LDB may be used as a beacon for the adaptive optics system. The collimated laser beam diameter may be approximately 1.5 mm at the eye's pupil, which may produce a diffraction-limited spot on the retina with a large depth of focus and is suitable for wavefront sensing. The beacon may be inserted into the system with a pellicle beam splitter PBS after the deformable mirror DM to avoid back scatter from the DM surface. It may be preferred to position the beacon before the scanners to avoid coherent speckle effects. Scanning may reduce speckle by averaging the wavefront measurement over the entire field of view, which may yield a more uniform wavefront correction.

The optical path may include four pupil planes (residing at the MEMS DM, the intermediate trial lens plane, the vertical scanner, and the horizontal scanner) imaged to the eye's pupil by a series of off-axis aspherical mirror telescopes. In this non-limiting example, design software from Zemax in Bellevue, Wash. (USA) was used to optimize the angles and surface placements to minimize the system aberrations. Most of the astigmatism in the system, which results from using spherical mirrors off axis, may be corrected using a cylindrical ophthalmic trial lens TL placed at the intermediate trial lens plane in FIG. 1. Also, the conjugate pupil plane may provide a convenient location to correct the eye's lower order aberrations—e.g., defocus and astigmatism—with standard ophthalmic trial lenses. These trial lenses may be spherical or cylindrical, for example.

The horizontal scanner HS of FIG. 1 may include a high frequency resonant scanner. In this configuration, a scanner was obtained from Electro-Optical Products Corp. of Glendale, N.Y. (USA). The horizontal scanner may be driven at a suitable frequency—in this case, sinusoidally at 15.1 kHz. However, the sinusoidal scan may cause image warp in the horizontal direction due to the constantly changing velocity of the horizontal scanner.

To remove warp from the images, it is possible to measure the horizontal warp with a linear line-pair grating (or other suitable device) placed at the focal plane of a model eye lens inserted at the eye's pupil plane (or inserted at another suitable location). Using a software algorithm, the retinal image may be stretched and compressed to reverse the effect of the scan warp. In this case, a Matlab (from Mathworks in Natick, Mass., USA) program was used to stretch and compress the retinal image. The algorithm may adjust the images to account for stretching caused by the use of a sinusoidal waveform. However, other suitable software programs or algorithms may be used to stretch and compress the retinal image to remove warp from the images.

A slow galvanometric scanner VS may be coupled to the horizontal scanner and driven in a sawtooth pattern at 26 Hz to give a vertical scan. Although a sawtooth waveform was used in this example, any waveform at a frequency that provides the desired scan results may be used. A suitable galvanometric scanner VS may be obtained from GSI Lumonics in Bedford, Mass. (USA). In this example, by adjusting both scanner amplitudes electronically, the imaging field of view can be varied from 1 to 3.5 degrees.

The adaptive optics system in FIG. 1 may include a MEMS deformable mirror DM and a Shack-Hartmann wavefront sensor WFS. Preferably positioned conjugate with the pupil plane of the eye, the WFS may include a lenslet array (obtainable from Adaptive Optics Associates in Cambridge, Mass., USA). In the example of FIG. 1, the lenslet array includes 18 mm focal length lenslets spaced at 328 µm and a digital camera (which may be obtained from Cohu in San Diego, Calif., USA). In this example, the camera may capture frames at 30 Hz and the wavefront aberration may be computed at 12 Hz for a 1004×1004 pixel array.

A 45 degree dichroic beam splitter DBS1 directs 95% of the light from the 904 nm laser diode to the WFS. The beam splitter DBS1 passes wavelengths less than about 830 nm to the imaging detectors. The MEMS DM (which may be obtained from Boston Micromachines Corp. in Boston, Mass., USA) may include a 4 µm stroke continuous membrane mirror with 144 electrostatic actuators arranged in a square or other suitable array (e.g., 12×12). The actuator spacing may be 400 µm, which results in a 4.8 mm diameter aperture. The mirror may be driven by a power supply, e.g., a high voltage power supply, that pulls down the membrane mirror surface under each actuator with applied voltage. The AO control may drive the DM using a suitable algorithm, such as a least squares inverse of the response matrix of the system.

Light for detection may be split by a cold mirror CM2, which may be adapted to pass the 830 nm light for reflectance imaging to the APD. A suitable APD may be obtained from Perkin Elmer in Vaudreuil, QC (Canada). An amplifier may be positioned proximate to the APD. The APD may have its own power supply, and a suitable power supply may be obtained from the Center for Visual Science. In fact, each element in the AOSLO 100 may have its own power source, if desired.

A photomultiplier tube PMT, obtained from Hamamatsu in Shizuoka-ken, Japan, may receive visible light. The PMT housing may include an electronic shutter (obtainable from Melles Griot in Rochester, N.Y. (USA)) to prevent damage from excess light. Appropriate dichroic mirrors and/or filters may be placed in front of the PMT for fluorescence imaging. Both detectors (e.g., the APD and the PMT) may have removable confocal pinholes CP placed at suitable locations, such as at retinal conjugate planes.

SLO system timing may be dictated by the synchronization signal generated by the horizontal scanner. The synchronization signal may be input to specialized control hardware (e.g., in the LEI box) that may be adapted to use the horizontal scanner signal to create a voltage ramp for stepping the vertical scanner. It may also be configured to generate the hsync and vsync signals for recreating the image in a frame grabber on the SLO PC.

The current signals from the APD and PMT may be converted to voltages using custom built and/or off the shelf transimpedance amplifiers (these may be obtained, for example, from Femto in Berlin, Germany). The converted current signals may then be connected to a custom built, three channel video signal conditioning board. The conditioning board is most useful for providing a blanking signal (e.g., no light), and may or may not be included in the system at the option of the designer.

The conditioning board may provide up to 40× gain per channel and may provide a computer adjustable blanking period for the incoming signal. Corresponding APD and PMT outputs from the video board may be connected to a 4-channel frame grabber. A suitable frame grabber may be obtained from Matrox in Dorval, QC (Canada). The hsync and vsync signals from the LEI hardware may be used by the frame grabber to generate a digital image (e.g., a 512×512 pixel digital image) from an incoming video signal at a suitable rate (e.g., a 26 Hz frame rate).

Low light levels from in vivo fluorescence imaging usually means that hundreds of frames are averaged to increase the signal to noise ratio. Inter-frame eye movements may preclude averaging some of the fluorescence frames together.

When ganglion cells are strongly labeled (e.g., a large injection of dye has been used) each fluorescence frame may contain sufficient spatial structure to cross-correlate. However, when ganglion cells and RPE cells are weakly labeled each fluorescence frame might not contain adequate spatial structure to cross correlate. In many cases of imaging the retina, especially but not limited to the case when the magnification is high, it is difficult if not impossible to obtain enough light in a short time interval to obtain a useful image. Safety considerations limit the amount of light that can be delivered to the retina without risk of light damage and the intrinsic reflectance or fluorescence of the retina is very low.

As one solution to the cross correlation problem, it is possible to use multiple detectors to acquire images of the retina in different spectral bands simultaneously. See, e.g., F. Reinholz et al., *Simultaneous Three Wavelength Imaging with a Scanning Laser Opthalmoscope*, Cytometry 37, 165-170 (1999) and P. M. Bischoff et al., *Simultaneous Indocyanine Green and Fluorescein Angiography*, Retina 15, 91-95 (1999), the contents of each of which are incorporated herein by reference. An alternative solution to the low signal problem is to simultaneously capture reflectance and fluorescence images using the APD and PMT detectors, respectively. Generally, each reflectance frame has a high enough signal to successfully estimate the image motion using a normalized cross correlation. It is possible to use a dual registration technique, where the image motions are calculated and appropriate shifts are applied to both the reflectance and fluorescence images.

Figure 29:
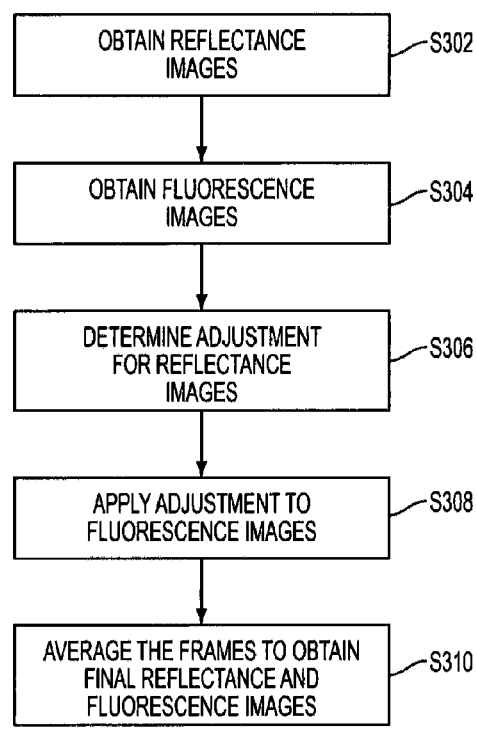
FIG. 29 illustrates an exemplary image processing method according to one aspect of the present invention.

An exemplary method of processing the images is illustrated in FIG. 29. As shown in FIG. 29, reflectance images may be obtained in step S302. In step S304, fluorescence images may be obtained. Preferably, steps S302 and S304 may occur simultaneously or approximately simultaneously. However, it is also possible to use a single detector to acquire both types of images, and the images may be time and/or frequency multiplexed.

Subsequently, in step S306, the amount of adjustment may be determined using the reflectance images. The reflectance images generally have a stronger light signal, which is why they may be preferred to use for determining the adjustment. However, other types of images may be used to determine the amount of adjustment. Generally, the amount of adjustment required may be determined, at least in part, based on the movement of the eye during imaging. Because it is nearly impossible for the eye to remain stationary (absent anesthesia) during imaging, it is preferred to correct for this eye movement in the images. For example, the first frame of the image series may be chosen as the reference. The distance that the retina (or other measuring point) moves from one image to the next may then be used to determine the adjustment in step S306. In step S308, the adjustment determined for the reflectance images may then be applied to the corresponding fluorescence images (since the images are obtained nearly simultaneously). By applying the adjustment from the reflectance images, it is possible to overcome the difficulties caused by the lower levels of light in the fluorescence images. In step S310, the adjusted frames may then be averaged to obtain final fluorescence and reflectance images.

The total processing time for one image may vary (e.g., from about 5 to about 60 minutes), depending on factors known to those of skill in the art, including: the number of frames, size of the cross correlation areas, and the speed of the processing computer(s). The number of frames used to create each image may vary as appropriate.

Although the exemplary AOSLO 100 described above uses fluorescence and reflectance imaging to obtain cell or vessel level images, other imaging techniques are within the scope of the present invention. For example, it is possible to use two CCD cameras capturing images at two different wavelengths. One of the series of images could be used to create a record of the eye's movements, while the other series of images would represent images of the desired area of investigation (e.g., the ganglion cells). Another exemplary alternative includes optical coherence tomography (OCT).

While the AOSLO 100 of FIG. 1 illustrates two light sources and two detectors, alternative configurations are within the scope of the present invention. For example, it is possible to have a configuration using a single light source and two detectors or a single light source and one detector. One detector could detect two separate series of images, the images being multiplexed such that a first frequency is detected at a first time and a second frequency is detected at a second time (etc.), such that two spectral bands are being obtained independently. Of course, configurations having more than two light sources and more than two detectors are also within the scope of the present invention.

This method can be used not only to correct for the effect of eye movements in translating and rotating the retinal image between frames, it could also be used to correct the warping of the retinal image caused by eye motion within each frame.

Figure 2:
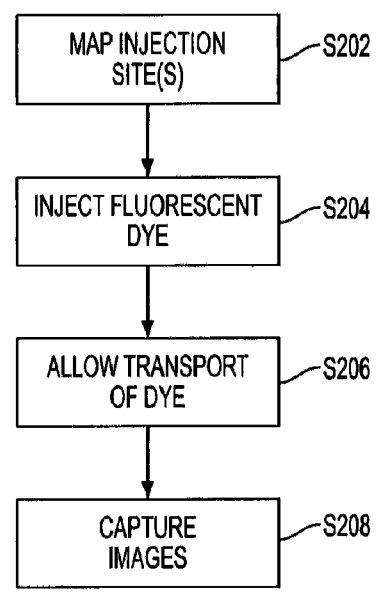
FIG. 2 illustrates a non-limiting example of a method for obtaining images according to the present invention.

FIG. 2 shows a non-limiting example of a method according to the present invention, in which fluorescent dye is injected into the subject to obtain images. In this application, the term "subject" includes humans as well as other animals. As shown in FIG. 2, the method may begin in step S202 by mapping the injection site(s). For example, tungsten or other suitable electrodes may be used to map the injection site. However, step S202 is optional.

In this example, the injection site was the right lateral geniculate nucleus (LGN) of the subject. Additionally, other injection sites known to those of skill in the art are also within the scope of the present invention. The other injection sites may or may not be mapped, at the discretion of the injection administrator.

In step S204, fluorescent dye was injected into the injection site (e.g., the LGN) of a subject. In this non-limiting example, injections (e.g., 200 nl to 800 nl) may be made under physiological guidance into selected locations in the LGN. It is possible to position the injections using a recording/injecting microelectrode while the subject maintains fixation. By selecting specific locations in the LGN, it is possible to have multiple tests on the same subject without interference.

In step S206, time is allowed to pass so that retrograde transport of the dye along retinal ganglion cell axons and into the soma of ganglion cells can occur. The amount of time allowed to pass may vary based on a number of factors, including the health of the subject and the type of dye used. In this particular example, five to six days may pass before imaging.

Additionally, at the option of the administrator, a chronic scleral search coil and head restraint system (see, e.g., A. Roorda et al., *Adaptive Optics Scanning Laser Opthalmoscopy*, Op. Express 10, 405-412 (2002), the contents of which are herein incorporated by reference) may be implanted. A chronic recording chamber (obtainable from Crist Instruments in Hagerstown, Md. (USA)) may also be implanted at a desired location. In this example, the chronic recording chamber was implanted at a location that permitted access to the LGN and other thalamic visual nuclei.

In this non-limiting example, individual injections used either rhodamine dextran or Alexa 594 conjugated to dextran. However, the injections are not limited to these compounds, and other compounds known to those of skill in the art are within the scope of the present invention. For example, fluorescein (which may be used in angiography), indocynanine green, and green fluorescent protein (GFP) are particularly suitable compounds. The compounds may be injected into the LGN, or into other locations, such as into the bloodstream. Other techniques for providing markers to the tissue to be imaged, such as oral administration, are also within the scope of this invention.

After step S206 shown in FIG. 2, the dyes may be excited so that images may be captured in step S208. In this non-limiting example, rhodamine dye may be excited with a 530 nm light and imaged with a 555 nm dichroic and 40 nm bandwidth filter centered at 593 nm. The Alexa 594 dye may be excited at 568 nm and imaged with a 583 nm dichroic and a 40 nm bandwidth filter centered at 624 nm.

To obtain images of the RPE cells, it is possible to excite lipofuscin, the intrinsic fluorophore contained in the RPE cell cytoplasm, using 568 nm light. Fluorescence may be imaged using a 583 nm dichroic and a 40 nm bandwidth filter centered at 624 nm. Generally, lipofuscin has a broad excitation range with a peak at 514 nm. The images illustrated in FIGS. 3(*a*)-7 were obtained by exciting at 568 nm. However, it is possible to obtain images by exciting at other wavelengths, as known to those of skill in the art. For example, it is possible to obtain images by exciting at 530 nm. Because the ANSI guide for the safe use of lasers allows 4.5 times greater exposure to 568 nm light than to 530 nm light, it may be advantageous to excite lipofuscin using a longer wavelength light.

From the registered RPE images, x-y coordinates of each RPE cell may be manually selected. NIH ImageJ software may be used as a part of the image processing procedure. A radial average of the two dimensional Fourier transform of the RPE cell mosaic may be computed. The peak of the annulus of the radial average may be defined as the modal cell spacing in the frequency domain. See, e.g., N. J. Coletta et al., *Psychophysical Estimate of Parafoveal Cone Spacing*, J. Opt. Soc. Am. A Opt. Image Sci. Vis. 3, 92-93 (1986), the entire contents of which are herein incorporated by reference. Cell density estimates may correspond to the number of cells divided by the area in which the cells were visible (e.g., where they were not obscured by the retinal vasculature).

In one embodiment of the present invention, images may be taken with simultaneous exposure of light at three wavelengths: about 530 nm or about 560 nm for fluorescence excitation, about 830 nm light for reflectance imaging, and about 904 nm light for wavefront measurement. In general, it is desirable to keep the combined photochemical and thermal exposure below the maximum permissible exposure limit (MPE) as stated in the ANSI guide for the safe use of lasers for extended sources for a two hour exposure time.

To image rhodamine dextran dye without adaptive optics, the retina may be simultaneously exposed to 120 µW at 530 nm, 436 µW at 830 nm for a 2 degree imaging field. To image lipofuscin containing RPE cells and Alexa 594 labeled ganglion cells with adaptive optics, the retina may be simultaneously exposed to 256 µW at 568 nm, 320 µW at 830 nm and 57 µW at 904 nm for a 2 degree imaging field. To image sodium fluorescein without adaptive optics, a 15 minute exposure time may be used and the retina may be exposed to 55 µW at 488 nm and 436 µW at 830 nm for a 3.5 degree imaging field. However, other exposures known to those of skill in the art are also within the scope of this invention.

As described above, one aspect of the invention provides for initiating retinal imaging about five days after dye injection. In that example, imaging continued for the following five months. During imaging, the subject may be anesthetized with isoflourane (e.g., 1-3 percent), pupils may be dilated with one to two drops of cyclopentolate (10 percent), a lid speculum may hold the imaged eye open, and a rigid gas permeable contact lens, which may be lubricated with a commercial wetting solution, may be used to protect the cornea.

The distribution of lipofuscin autofluorescence across the retina has been well established and has been linked to a number of retinal diseases. However, it was not previously possible to clearly identify individual RPE cells in vivo. The ability to take in vivo images of the RPE cell mosaic provides a means to study the morphology of normal and diseased cells, as well as their role in retinal diseases and their associated therapies.

As an additional non-limiting aspect of the invention, two photon microscopy may be used to obtain images of RPE cells in vivo through the sclera. Two photon microscopy enables functional imaging in vivo by spectrally separating the imaging and visible range stimulation wavelengths. This technique has advantages of histological studies, and may be improved upon by the use of high resolution adaptive optics to image through they eye's own optics where the imaging location is not limited to the peripheral retina (as it may be when imaging through the sclera). The ability to capture in vivo images of the RPE cell mosaic provides a way to study the morphology of normal and diseased cells, as well as their role in retinal diseases and associated therapies.

In a non-limiting aspect of the invention, the chronic head restraint system was used to align the subject's eye with the imaging system. This was accomplished by connecting the head post to a goniometer and rotation mount centered on the nodal point of the eye that allowed the retinal imaging location to be shifted with minimal misalignment of the eye's pupil. A motorized three axis translation stage obtained from Velmex in Bloomfield, N.Y. (USA) was used to align the eye to the pupil plane of the AOSLO. Other methods of positioning the eye for imaging are also within the scope of this invention.

In one non-limiting aspect of the invention, it is possible to assume that the subject's retina has the optical properties of the LeGrand model eye for the human. See, e.g., G. Wyszecki et al., *Color Science: Concepts and Methods, Quantitative Data and Formulas*, John Wiley & Sons, Inc., New York (1982), the entire contents of which are incorporated herein by reference. Using these assumptions, it is possible to convert angular measures of the dimensions of imaged retinal structures to physical size.

Additionally, it is possible to rescale all or some of the subject's eye dimensions by measuring the axial length of the subject's eye. In the subject used for the images obtained in FIGS. 3(a)-7, the eye had an axial length of 21.97 mm, which was measured using an IOLMaster obtained from Carl Zeiss Meditec in Jena, Germany. By contrast, the LeGrand model eye has a 24.2 mm axial length. Thus, it is possible to adjust the retinal spatial-angular conversion based on the measurements. In this example, the retinal spatial-angular conversion may be reduced from 291 μm/deg for the model to 264 μm/deg for the particular subject.

In this non-limiting example, the images were taken on the left eye of the subject. The lower order correction of defocus and astigmatism resulted in an average root means square (RMS) wavefront error of about 0.2 μm to about 0.3 μm over a 5.5 mm pupil as measured by the wavefront sensor. AO correction may be performed over a 5.55 mm pupil with typical residual RMS wavefront error of 0.05 μm to 0.12 μm.

Injections to the upper (P) and/or lower (M) layers of the LGN yielded excellent dye labeling of retinal ganglion cells. FIGS. 3(a)-3(d) illustrate ganglion cell bodies and axons labeled with either rhodamine dextran or Alexa 594 dyes from different regions of the retina.

Figure 3A:
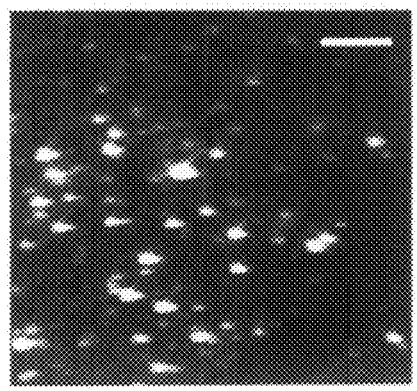
FIGS. 3(a)-3(d) illustrate ganglion cell bodies and axons imaged according to a non-limiting aspect of the present invention.

FIG. 3(a) was taken at an eccentricity of approximately 17 degrees nasal and 5 degrees inferior, just below the optic disk. FIG. 3(a) shows labeled axons extending up and to the right from some of the labeled cells. By enhancing the contrast of the image, axons become more visible, which causes cell bodies to appear saturated. FIG. 3(a) was constructed from 500 frames.

Figure 3B:
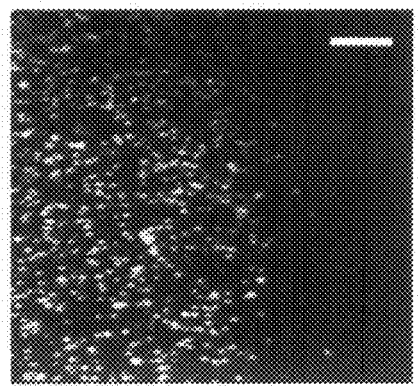

FIG. 3(b) was taken on the vertical meridian of the retina, approximately 10 degrees inferior from the fovea. FIG. 3(b) shows dense labeling of ganglion cells in the left half of the image which project to the injected LGN. The unlabeled ganglion cells on the right side of the image project to the opposite LGN. FIG. 3(b) was constructed from 200 frames.

Ganglion cells in both 3(a) and 3(b) were labeled with rhodamine dextran dye and the images were taken before the adaptive optics and dual registration techniques had been implemented. The scale bars for FIGS. 3(a) and 3(b) were 100 μm.

Figure 3C:
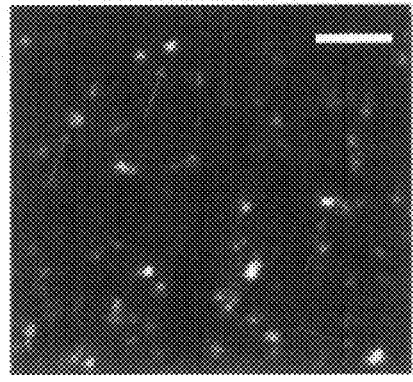
Figure 3D:
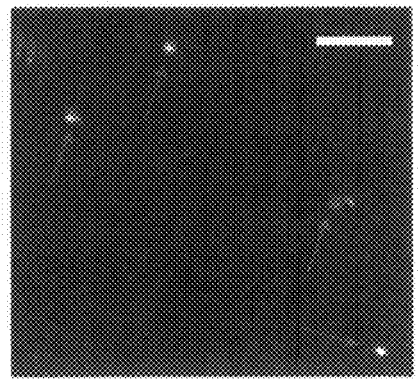

FIGS. 3(c) and 3(d) show the persistence of the dye in cells labeled with Alexa 594 dye. FIG. 3(c) was taken at an eccentricity of approximately 10 degrees infero-nasal. FIG. 3(c) was taken 37 days after the injection and FIG. 3(d) was taken 77 days later. FIG. 3(d) was taken at the same position as FIG. 3(c). The four ganglion cells marked by arrows can be seen in both images. Generally, after a particularly dense injection, label could be seen five months after the injection. FIGS. 3(c) and 3(d) were constructed from 512 frames and 1000 frames, respectively, and their scale bars were both 50 μm.

In the non-limiting example of FIG. 3(d), the adaptive optics were used to focus through the ganglion cell layer to find the best plane of focus. This determination was made in steps of 0.1 diopters (D).

Ganglion cells labeled with rhodamine dextran dye exhibited a brightening effect when the retinal light exposure was increased by three times. The effect was apparent while cells were being imaged, and the brightening could be enhanced by adjusting the scanner amplitudes to illuminate only a small 1 degree patch.

Figure 4A:
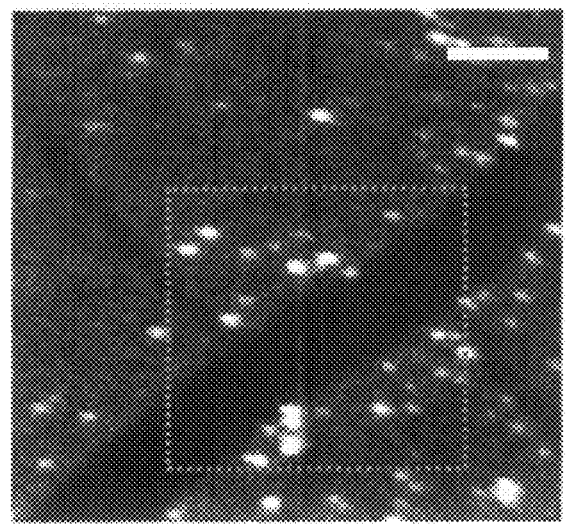
FIGS. 4(a) and 4(b) illustrate cells imaged according to another non-limiting aspect of the present invention.
Figure 4B:
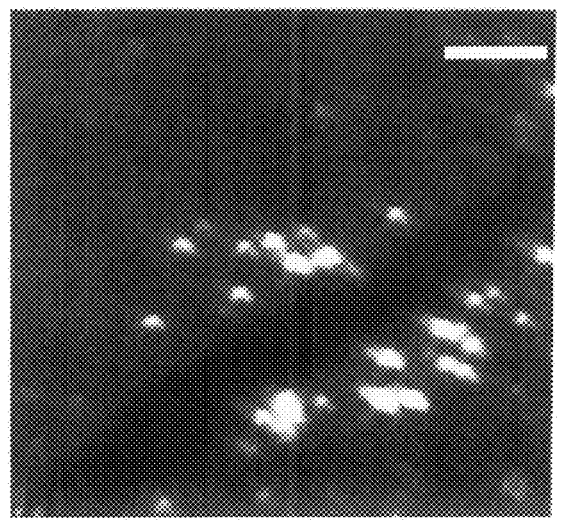

FIGS. 4(a)-4(b) show the result of exposing one section of the retina to increased light for approximately 20 minutes. Both FIGS. 4(a) and 4(b) were taken without adaptive optics or dual registration, and 300 frames were used to create both images. Scale bars are 100 μm in both figures.

FIG. 4(a) was located at an eccentricity of approximately 19 degrees nasal and 7 degrees inferior and shows ganglion cells labeled with rhodamine dextran dye. The image was taken before exposure to intense light, and the cells were excited at 530 nm.

After exposure, shown in FIG. 4(b), the exposed cells were substantially brighter than cells that were not exposed. The extent of the exposure was larger than 1 degree due to eye motion. The cells in FIG. 4(b) were excited with 530 nm light.

Figure 5A:
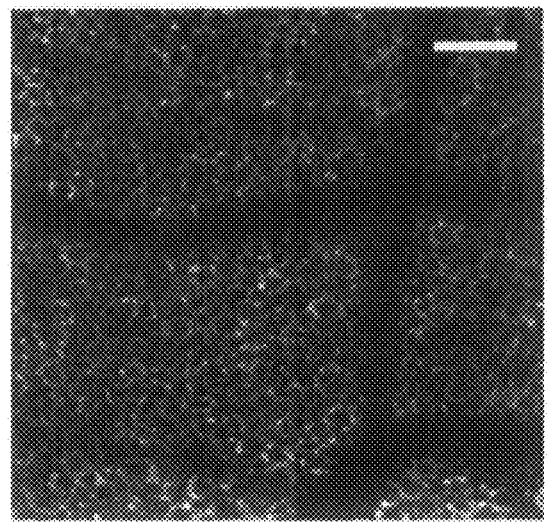
FIGS. 5(a) and 5(b) illustrate RPE cells imaged according to yet another non-limiting aspect of the present invention.
Figure 5B:
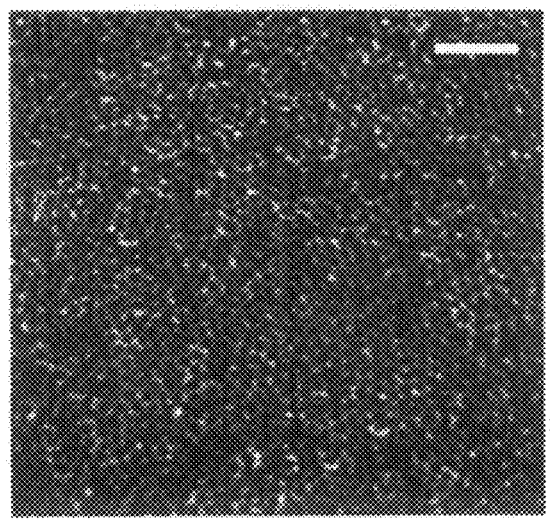

Individual RPE cells were imaged by exciting the lipofuscin fluorophores that are found naturally in RPE cell cytoplasm. FIG. 5(a) shows the RPE mosaic at approximately 10 degrees infero-nasal—at the same location as the ganglion cells illustrated in FIGS. 3(c) and 3(d). FIG. 5(b) illustrates the RPE mosaic at the fovea. Both FIGS. 5(a) and 5(b) were captured using the dual registration technique described above.

In both FIGS. 5(a) and 5(b), the RPE cell mosaic appears in a honeycomb pattern, possibly because only the cytoplasm surrounding the nuclei of the cells may contain fluorescent lipofuscin. It may be possible to have considerable variability in the amount of fluorescence observed in neighboring RPE cells. See, e.g., J. M Burke et al., *Mosaicism of the Retinal Pigment Epithelium: Seeing the Small Picture*, Mol. Interv. 5, 241-249 (2005), the contents of which are incorporated herein by reference.

Using the adaptive optics system illustrated in FIG. 1, it is possible to gradually adjust the focus to find an optimal plane of focus for the RPE cells. As a non-limiting example, it is possible to perform a through focus series in 0.1 diopter steps to locate a preferred plane of focus.

Figure 6A:
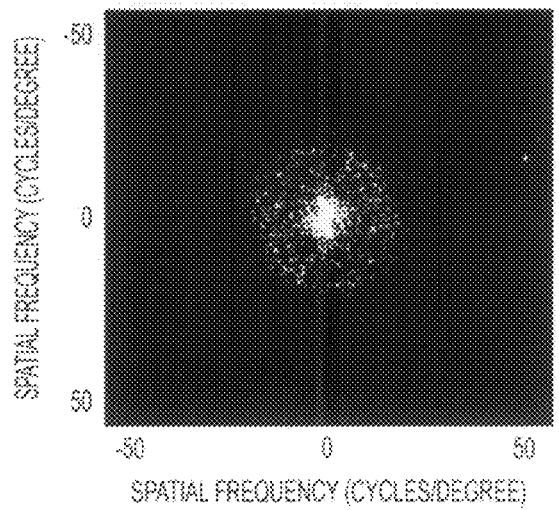
FIGS. 6(a) and 6(b) illustrate two dimensional power spectrums obtained according to non-limiting aspects of the present invention.
Figure 6B:
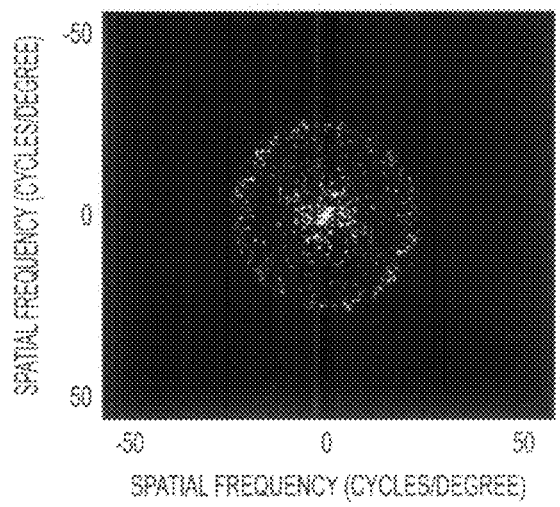

As shown in FIGS. 5(a) and 5(b), the RPE cells may be roughly triangularly packed. Most cells typically have six immediate neighbors. FIGS. 6(a) and 6(b) illustrate the radial power spectrum. In FIGS. 6(a) and 6(b), an annular peak of 15 cycles/degree was measured at 10 degrees eccentricity. Correspondingly, 22.8 cycles/degree were measured at the fovea. At 10 degrees eccentricity, the average modal cell spacing was 17.6 μm, while at the fovea the modal cell spacing was 11.6 μm. At 10 degrees eccentricity, the cell density may be 2,876 cells/mm$^2$ and 6,339 cells/mm$^2$ at the fovea.

Using the methods described in N. J. Coletta et al., *Psychophysical Estimate of Parafoveal Cone Spacing*, J. Opt. Soc. Am. A Opt. Image Sci. Vis. 3, 92-93 (1986), the contents of which are incorporated herein by reference, a perfect triangular spacing would yield modal spacing of 17.4 μm for the same density at 10 degrees and 11.7 μm at the fovea.

In comparison, Snodderly et al. measured the RPE density of eight rhesus monkeys and reported an average of 3,997+/−551 cells/mm$^2$ at 9 degrees eccentricity and 7,139+/−1193 cells/mm$^2$ at the fovea. See, e.g., D. M. Snodderly et al., *Retinal Pigment Epithelial Cell Distribution in Central Retina of Rhesus Monkeys*, Invest. Opthalmol. Visual Sci. 43, 2815-2818 (2002), the contents of which are incorporated herein by reference.

In one non-limiting example, measurements of RPE and cone density were performed at 10 degrees eccentricity, and cone density was found to be 13,275 cells/mm$^2$, which was similar to previous measurements of cone density in three macaque nemestrina monkeys of 12,000 cones/mm$^2$ on average. See, e.g., O. Packer et al., *Photoreceptor Topography of the Retina in the Adult Pigtail Macaque (Macaca-Nemestrina)*, J. Comp. Neurol. 288, 165-183 (1989), the contents of which are incorporated herein by reference. In this example, the measured density of cones at 10 degrees eccentricity is 4.6 times greater than that of RPE cells, making RPE cells easily distinguishable from cones.

Figure 7:
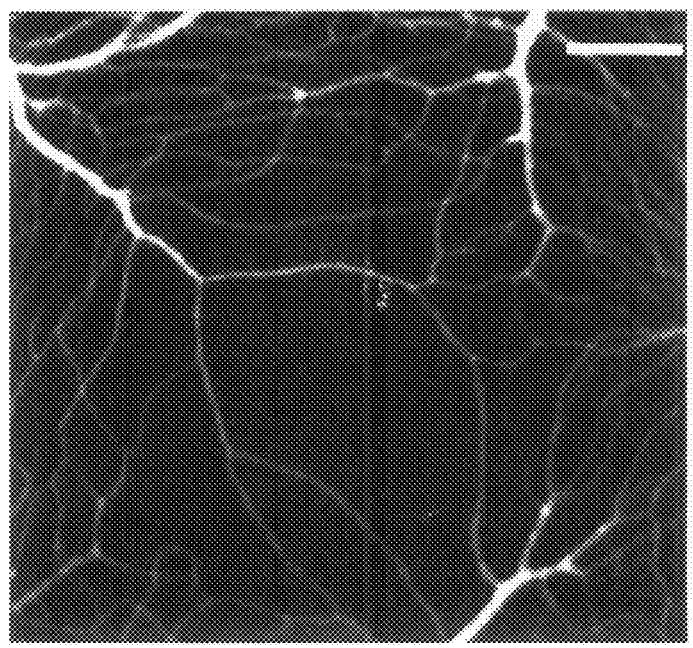
FIG. 7 illustrates a non-limiting example of an image of capillaries in the area surrounding the foveal avascular zone.

To perform fluorescein angiography of the foveal avascular zone, the subject was given a 0.7 ml intravenous injection of 10 percent sodium fluorescein dye. Using 488 nm excitation, a 495 nm long pass dichroic and 35 nm band pass filter centered at 520 nm, at a 3.5 degree field of view, the complete capillary bed surrounding the avascular zone of the subject was visible, as shown in FIG. 7. The image of FIG. 7 was taken without the use of adaptive optics, and the preferred focus was achieved using trial lenses. In FIG. 7, 1918 fluorescence frames were dual registered.

In FIGS. 3(a)-7, the images were obtained during the development of the adaptive optics system shown in FIG. 1. The images were obtained from the eye of a subject with best corrected RMS wavefront error of 0.2 to 0.3 µm as measured by a wavefront sensor.

Figure 8:
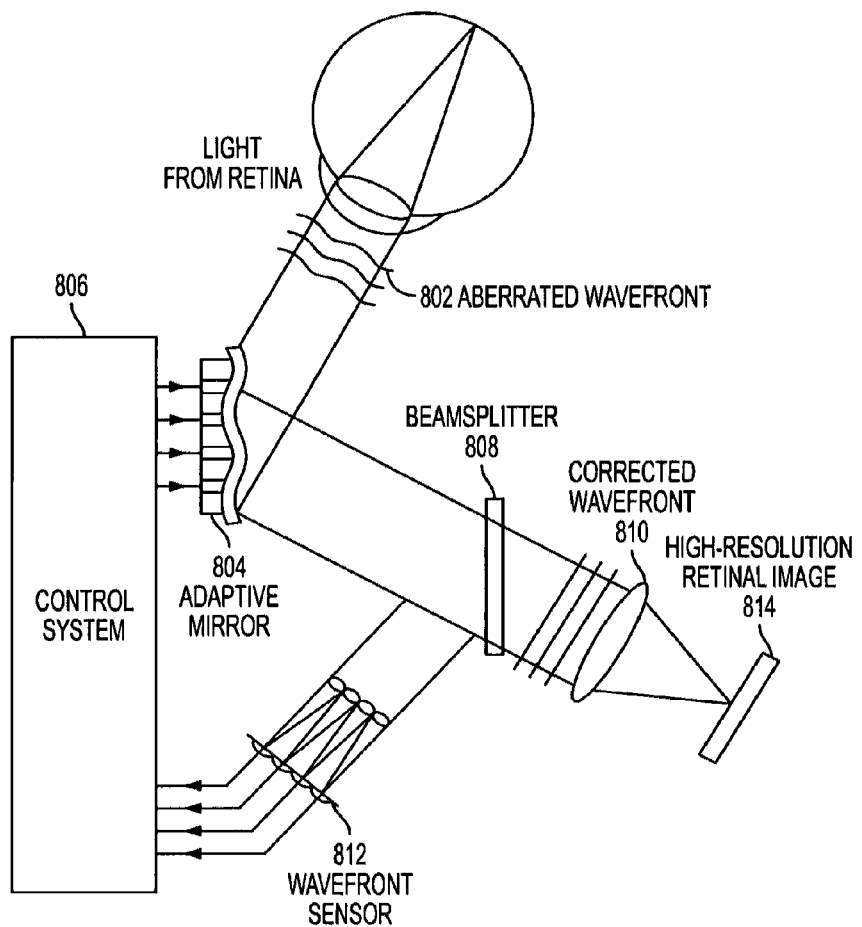
FIG. 8 illustrates an exemplary adaptive optics retinal imaging system.

FIG. 8 provides another non-limiting example of a system for adaptive optics retinal imaging. As shown in FIG. 8, light from the retina may be reflected onto an adaptive mirror 804. Adaptive mirror 804 receives an input from the control system 806 that specifies a voltage for each actuator in the mirror with the entire set of actuator voltages updated a video rates based on the measured displacements of the spots in the wavefront sensor. The adaptive mirror 804 also transmits light through the beamsplitter 808, and a corrected wavefront 810 is transmitted to obtain a high resolution retinal image 814. Light from the beam splitter 808 is also transmitted to the wavefront sensor 812.

Figure 9:
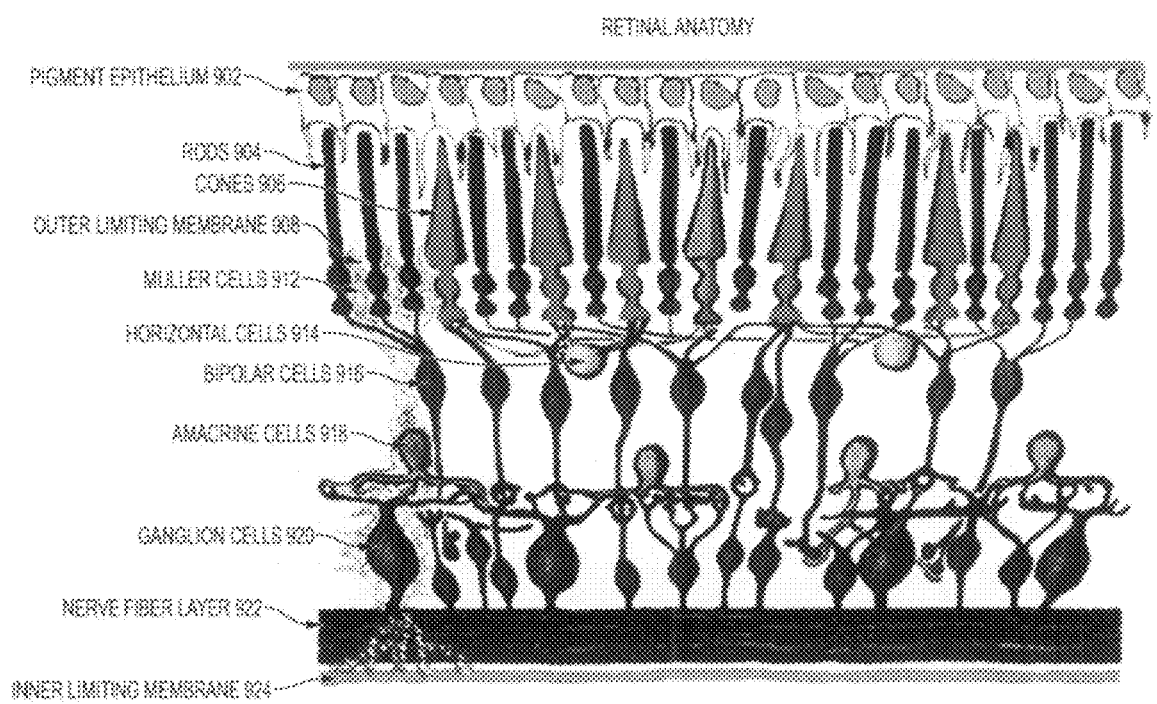
FIG. 9 illustrates an example of retinal anatomy.

FIG. 9 illustrates an example of the retinal anatomy. As shown in FIG. 9, the retinal anatomy may include: pigment epithelium 902, rods 904, cones 906, outer limiting membrane 908, Müller cells 912, horizontal cells 914, bipolar cells 916, amacrine cells 918, ganglion cells 920, nerve fiber layer 222 and inner limiting membrane 924.

Figure 10:
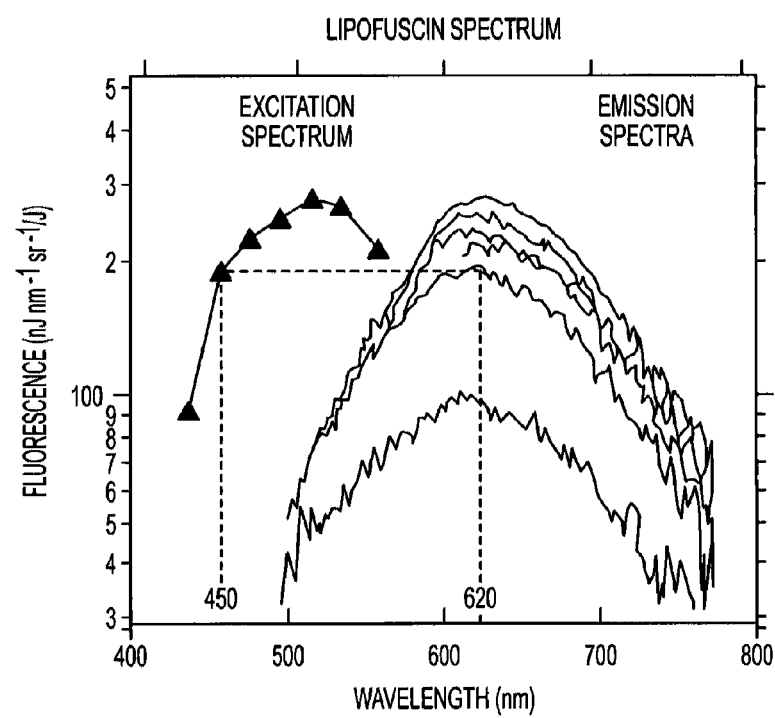
FIG. 10 provides an exemplary illustration of the lipofuscin spectrum.

FIG. 10 illustrates an exemplary lipfuscin spectrum. As shown in FIG. 10, lipofuscin has a broad excitation and emission spectra. In the example of FIG. 10, the peak excitation may be seen at 510 nm and the peak emission may be seen at 631 nm. FWHM (full width at half maximum) may be seen at 167 nm.

Figure 11A:
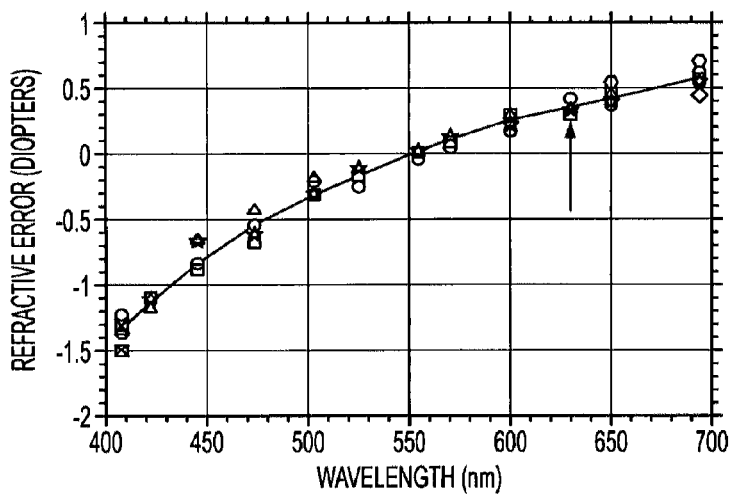
FIGS. 11(a) and 11(b) illustrate longitudinal chromatic aberration of the eye.
Figure 11B:
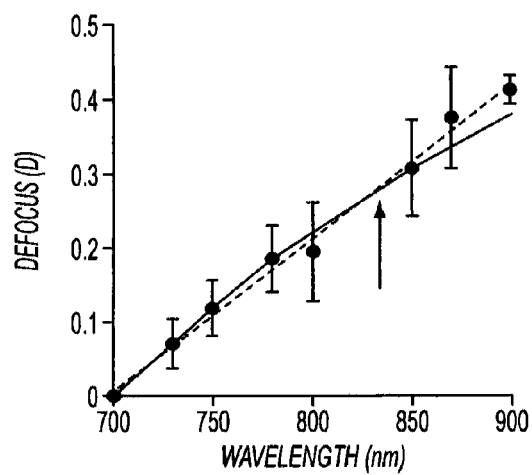

FIG. 11(a) illustrates refractive error (in diopters) as a function of wavelength. FIG. 11(b) illustrates defocus as a function of wavelength. Generally, the eye has chromatic aberration depending upon which wavelengths enter the eye. When the amount of chromatic aberration is known, input light can be correctly focused to the specific retinal layer desired.

Figures 12A, 12B:
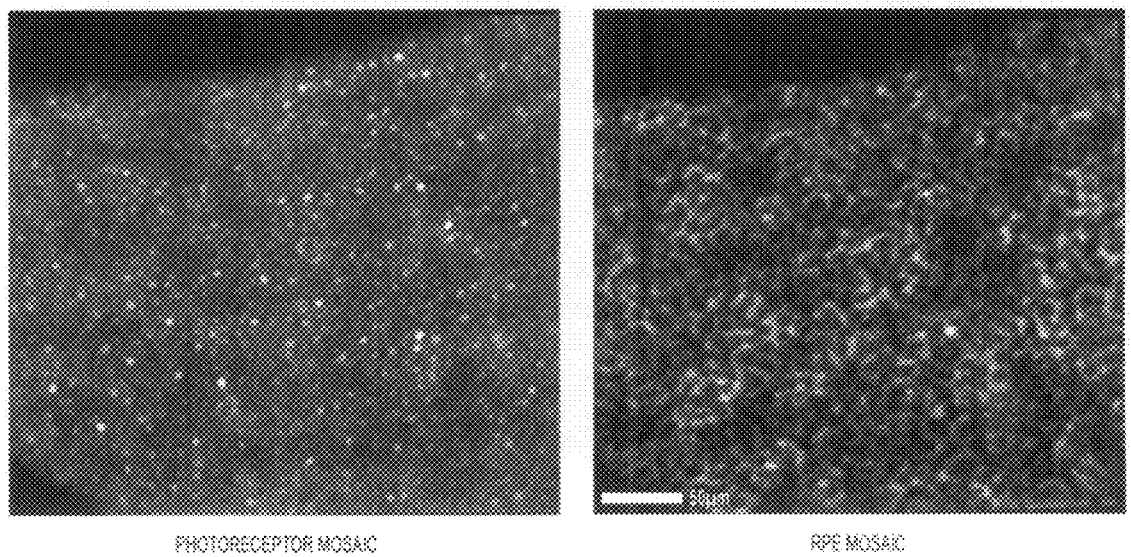
FIGS. 12(a) and 12(b) show an exemplary photoreceptor mosaic and an exemplary RPE mosaic, respectively.
Figure 13A:
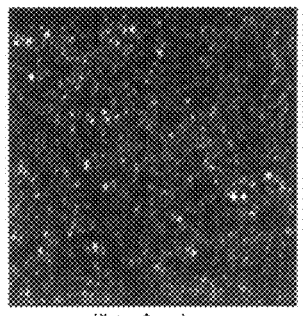
FIGS. 13(a)-13(f) illustrate exemplary photoreceptor and RPE mosaics obtained using the exemplary imaging techniques of the present invention.
Figure 13B:
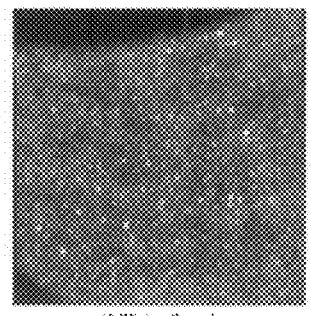
Figure 13C:
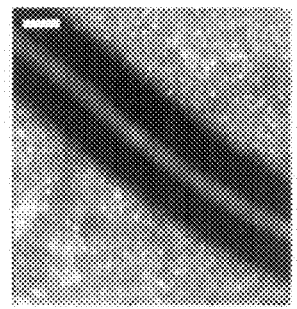
Figure 13D:
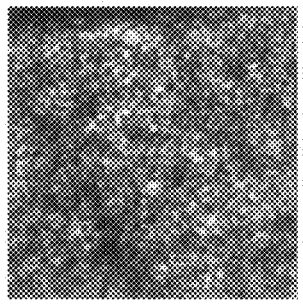
Figure 13E:
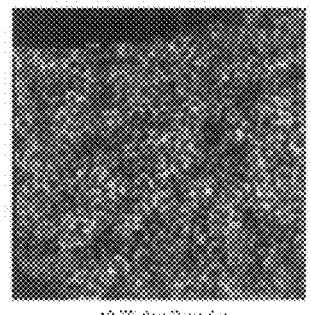
Figure 13F:
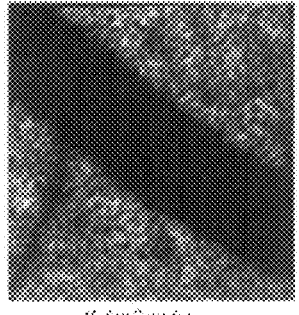

FIGS. 12(a) and 12(b) illustrate a photoreceptor mosaic and an RPE mosaic obtained according to the methods described above. FIG. 12(a) illustrates photoreceptor reflectance and FIG. 12(b) illustrates RPE fluorescence).

FIGS. 13(a)-13(f) illustrate two series of images. The first series of images (a)-(c) illustrates reflectance imaging of the photoreceptor layer obtained at 10 degrees, 13.75 degrees and 15 degrees superior to the fovea, respectively. The second series of images illustrates fluorescence imaging of the RPE at the same respective locations.

FIG. 14(a) illustrates an RPE mosaic in the spatial domain obtained at 13.75 degrees superior to the fovea. FIG. 14(b) illustrates the mosaic of FIG. 14(a) in the frequency domain after the data was processed using a Fast Fourier Transform. FIG. 14(c) is a table that provides data calculated based on images obtained using the method of the present invention.

Figure 15A:
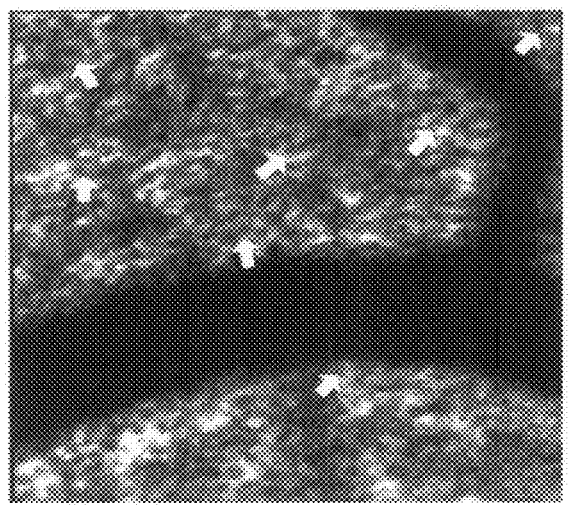
FIGS. 15(a) and 15(b) represent images of RPE cells obtained at different times.
Figure 15B:
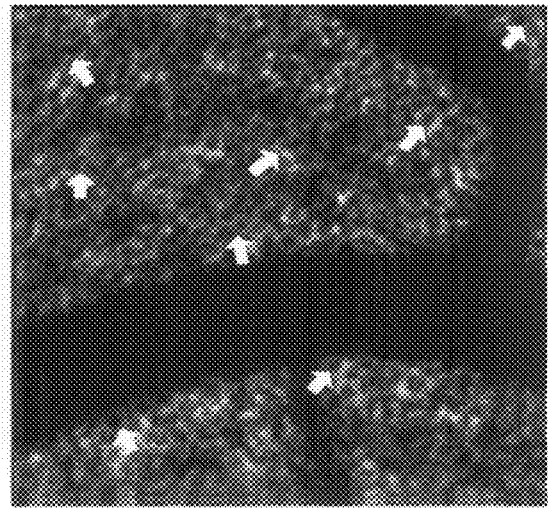

FIGS. 15(a) and 15(b) provide images of the same RPE mosaic. Before the images of FIG. 15(b) were obtained, 42 days lapsed after the images of FIG. 15(a) were obtained. These images have a cross correlation coefficient of 0.95, and the scale bar is 50 µm.

Figure 16:
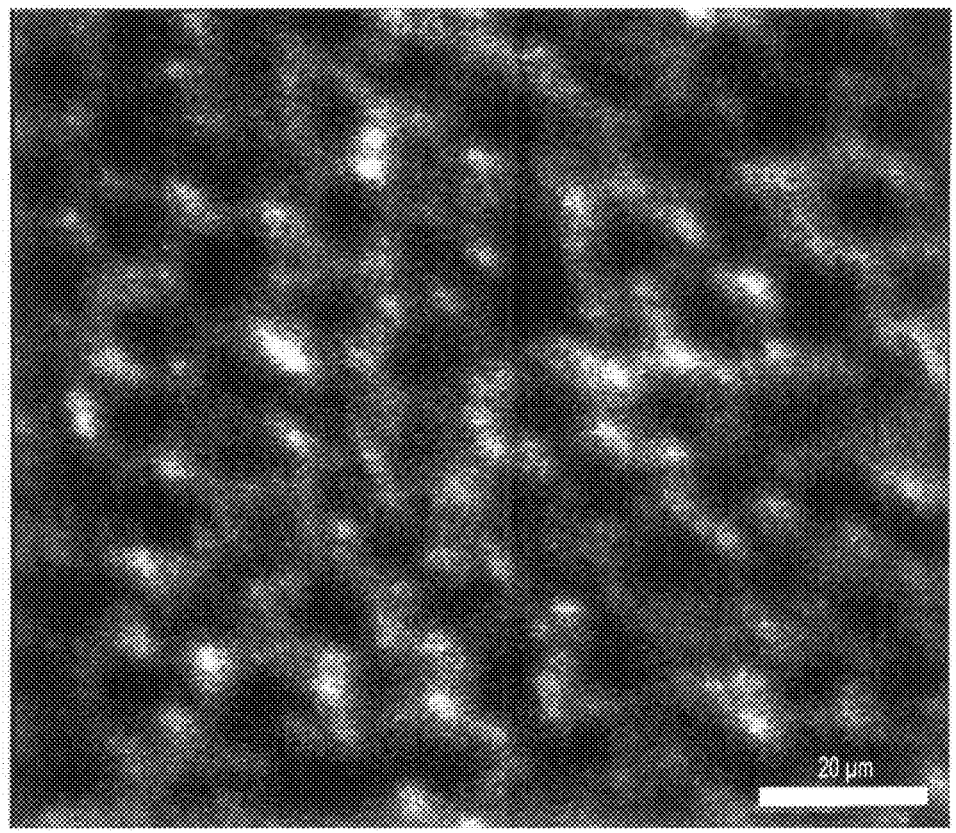
FIG. 16 illustrates exemplary subcellular RPE features using autofluorescence imaging.
Figure 17:
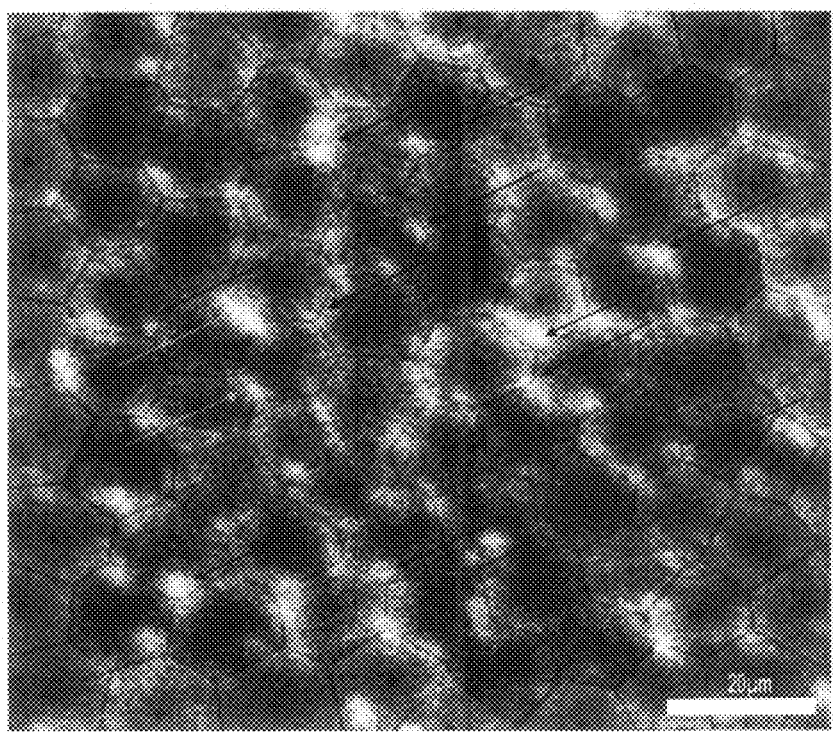
FIG. 17 also illustrates exemplary subcellular RPE features using autofluorescence imaging.

FIG. 16 illustrates subcellular features of the RPE that were obtained using autofluorescence imaging. FIG. 17 provides a detailed illustration of subcellular RPE features obtained by autofluorescence imaging. In FIG. 17, the black arrows point to areas that have three cell borders, whereas the orange arrows are pointing to two cell borders. The bright spots at the points of the arrows are caused by the autofluorescent materials (e.g., lipofuscin granules), which tend to be located at cellular borders. The color schemes throughout the figures remain consistent. The vertices and midpoints with arbitrary numbers show that the intensity of the autofluorescence signal is higher at the vertices of the cells than the midpoints of the cells, meaning that in this example, the lipofuscin granules were located more often at the vertices of the cells.

Figure 18A:
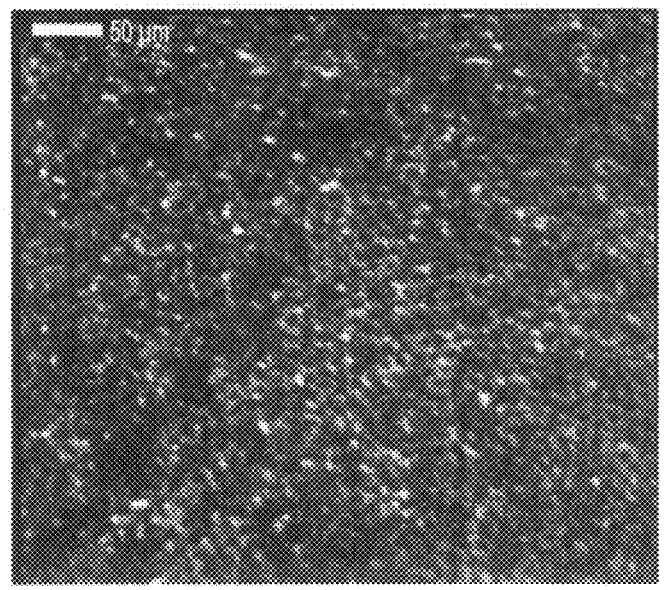
FIGS. 18(a) and 18(b) illustrate exemplary aspects of the RPE mosaic and eccentricity at different locations.
Figure 18B:
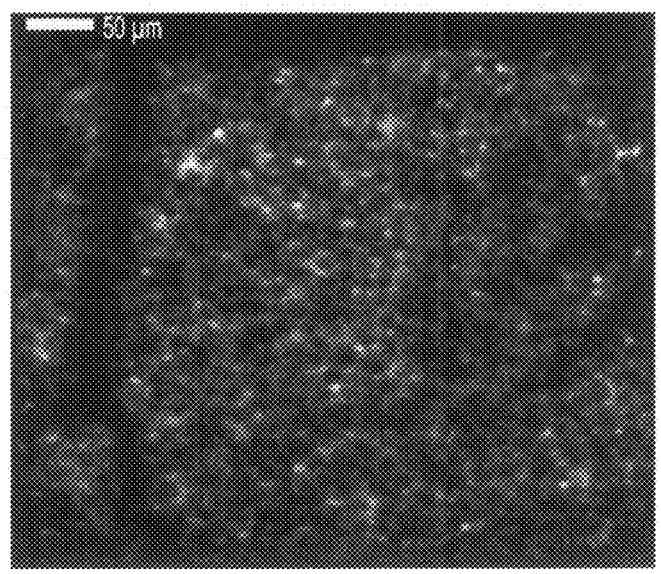
Figure 19A:
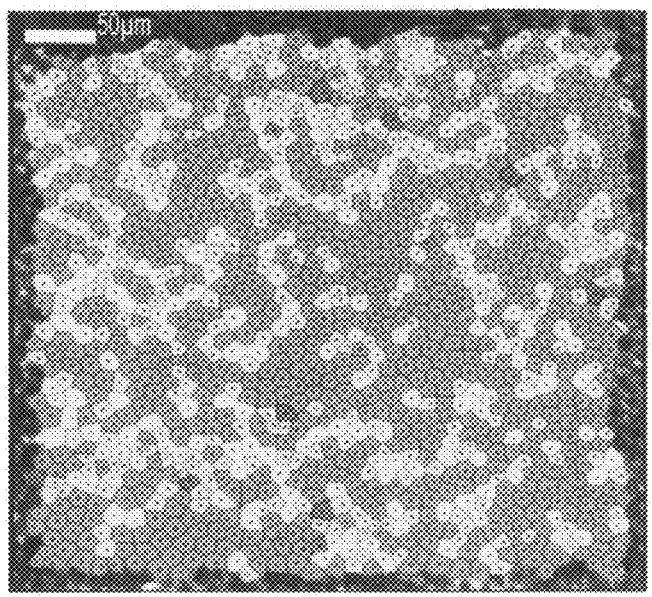
FIGS. 19(a) and 19(b) also illustrate exemplary aspects of the RPE mosaic and eccentricity at different locations.
Figure 19A:
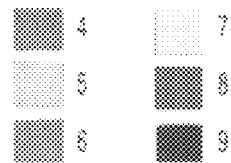
Figure 19B:
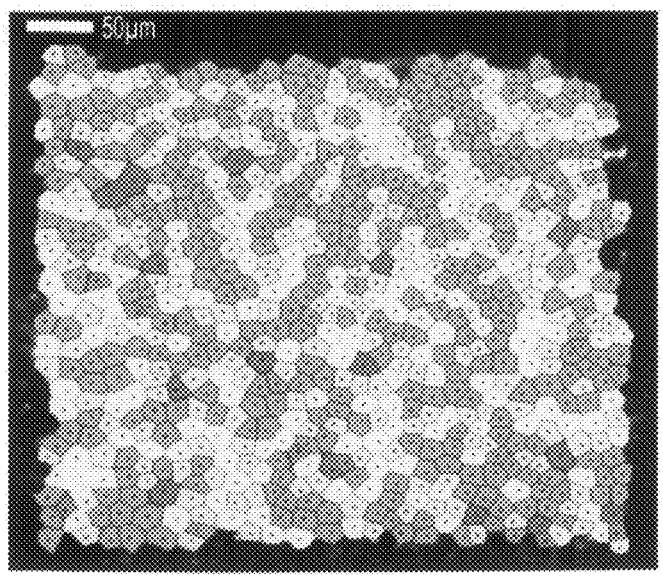
Figure 19B:
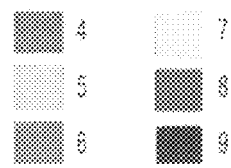

FIGS. 18(a) and 18(b) represent RPE mosaics obtained at 2 degrees and 8 degrees from the fovea, respectively. FIGS. 19(a) and 19(b) provide a more detailed explanation of the images pictured in FIGS. 18(a) and 18(b). As can be seen from FIGS. 19(a) and 19(b), the configuration of the RPE mosaic varies based on the distance from the fovea. In a patient with retinal disease (e.g., age related macular degeneration or other diseases), the RPE mosaic may have a larger number of 4/5 cells and 7/8 cells, as compared to the large number of 6 cells shown in these figures.

Figure 20:
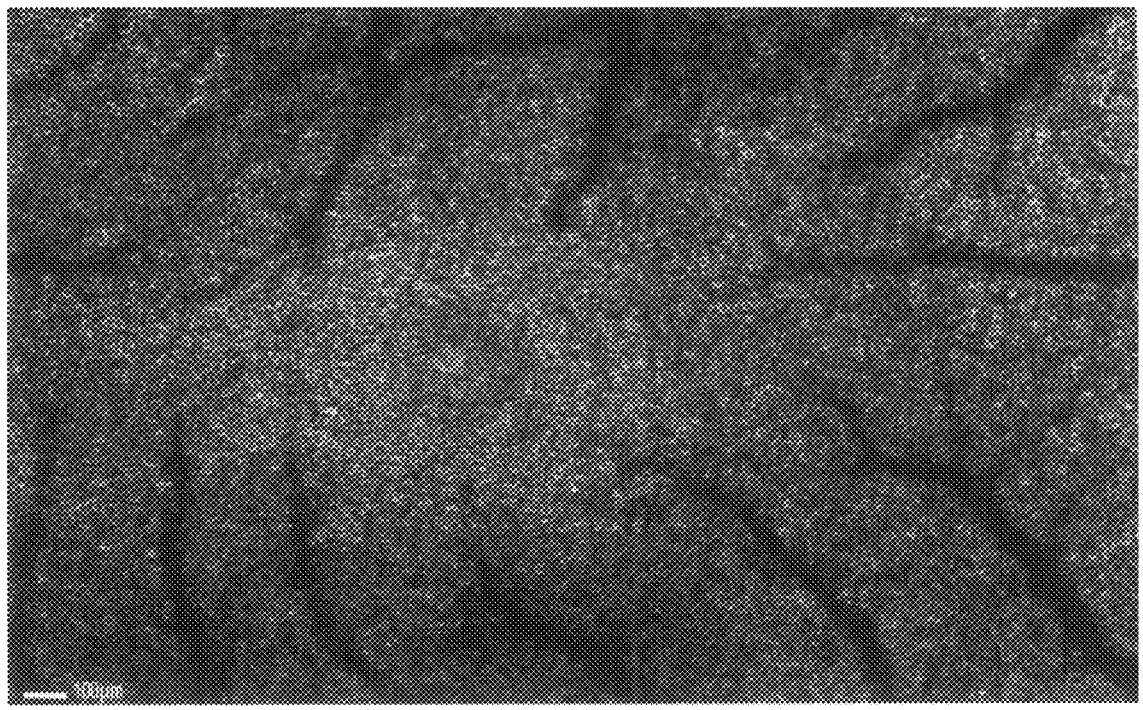
FIG. 20 illustrates an exemplary RPE cell mosaic.
Figures 21A, 21B, 21C:
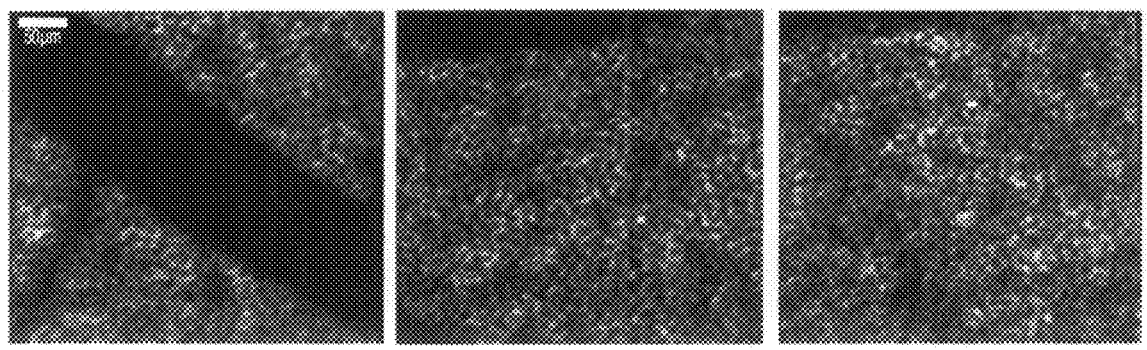
FIGS. 21(a)-21(c) illustrate exemplary aspects of human RPE cell mosaics and eccentricity.

FIG. 20 illustrates an RPE cell mosaic at the fovea of a Macaque retina. FIGS. 21(a)-21(c) illustrate human RPE cell mosaics and eccentricity. The data used to generate FIGS. 21(a)-21(c) uses the same RPE images as shown in FIGS. 12(a)-12(f). The images in FIGS. 21(a)-21(c) were obtained at different locations from the fovea, as described in the figure. Each different location yielded different cell densities, as described in the figures. According to a non-limiting aspect of the present invention, imaging is possible up to at least 20 degrees from the fovea (e.g., anywhere in the macula). Other locations for imaging known to those of skill in the art are also within the scope of the present invention.

Figure 22:
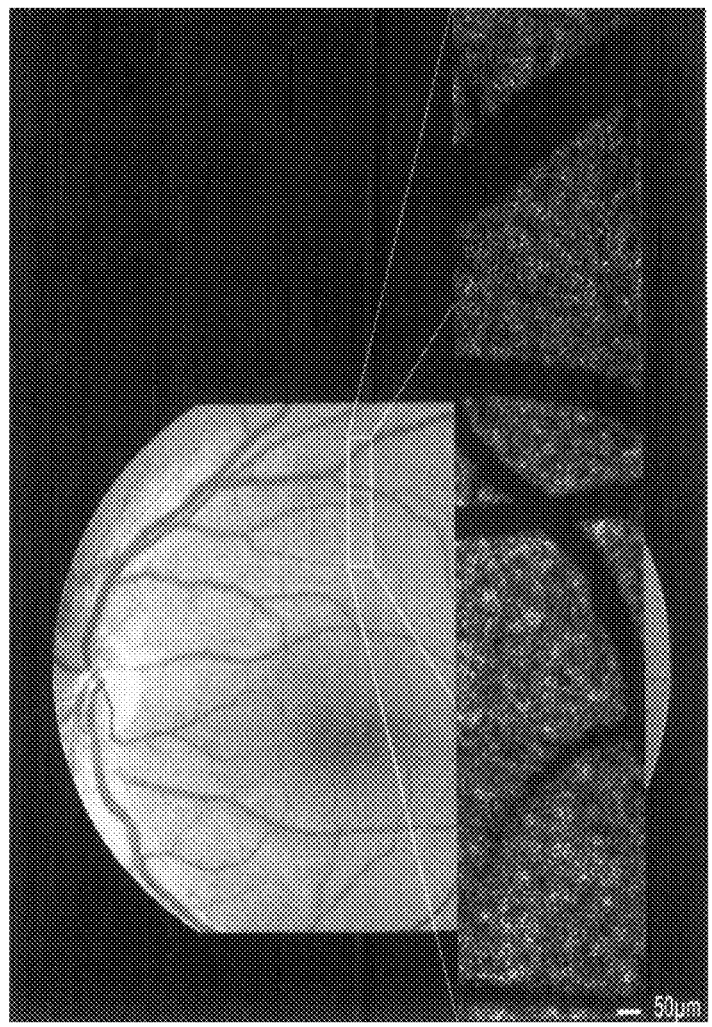
FIG. 22 illustrates imaging the RPE at multiple retinal locations.

One non-limiting aspect of the present invention provides for imaging the RPE at multiple retinal locations. As shown in FIG. 22, some of the images illustrated elsewhere in this application were obtained from the rectangular area superimposed on the traditional fundus image. The rectangular cell level image was obtained by stacking a plurality of different images, each image being obtained from the rectangle that is superimposed on the fundus image.

Figure 23:
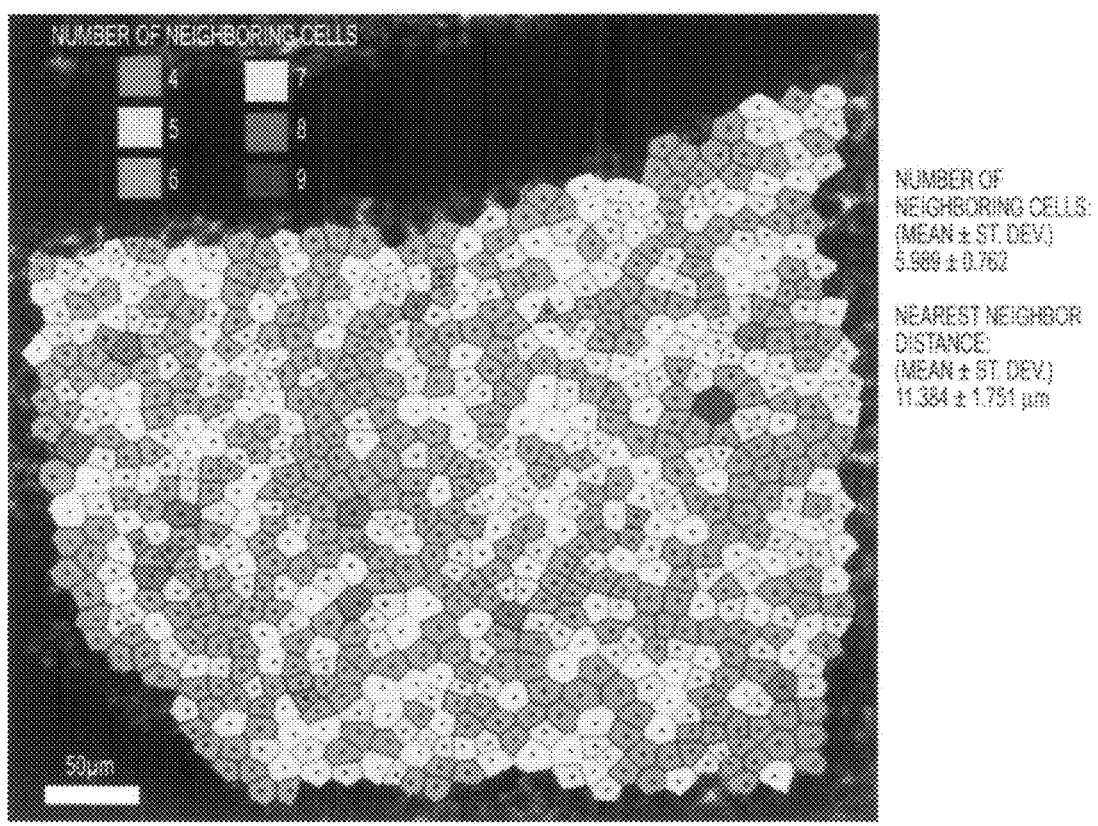
FIG. 23 illustrates an exemplary characterization of the RPE cell mosaic.
Figure 24:
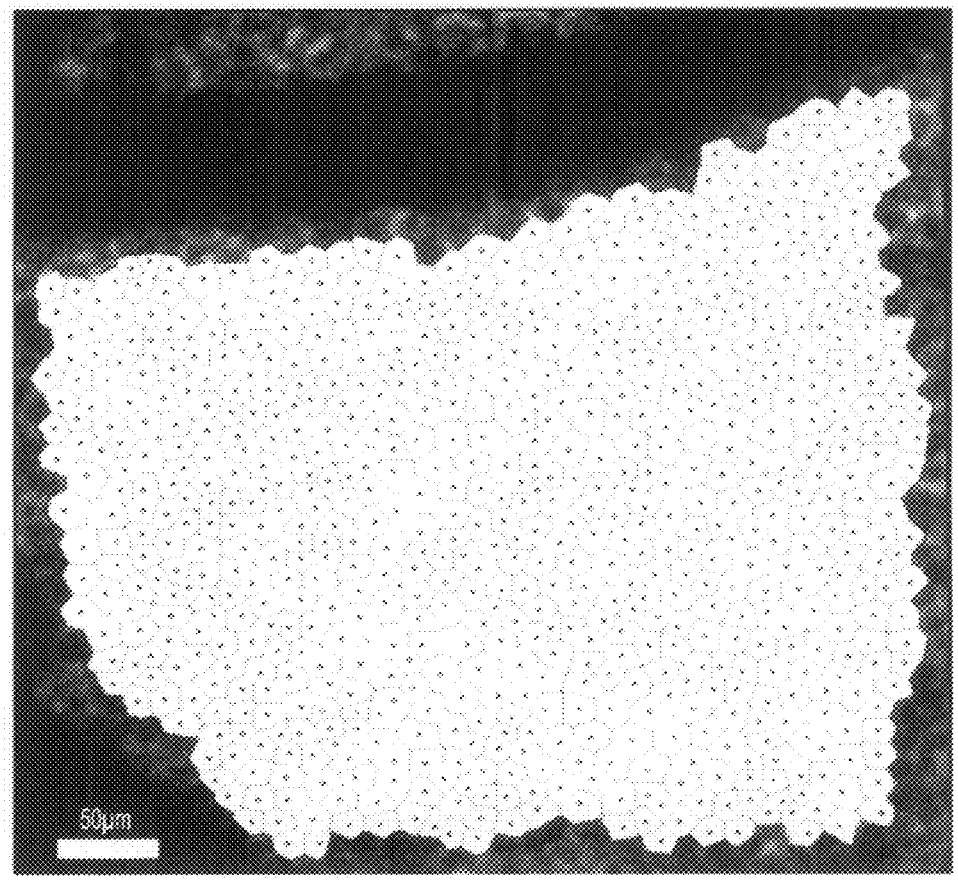
FIG. 24 also illustrates an exemplary characterization of the RPE cell mosaic.
Figure 25:
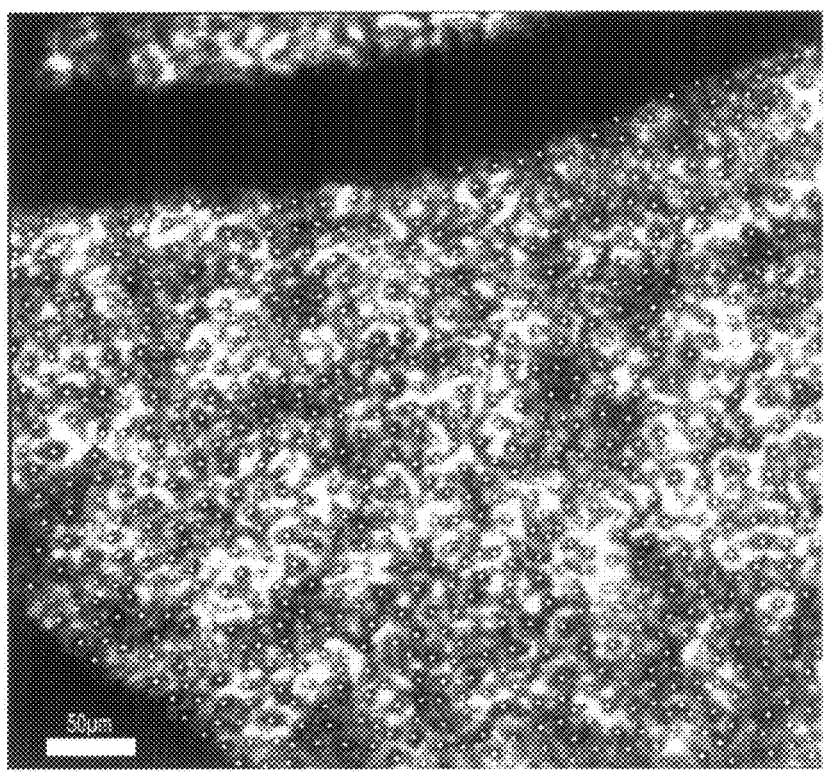
FIG. 25 illustrates another exemplary characterization of the RPE cell mosaic.

FIGS. 23-25 provide exemplary illustrations of RPE cell mosaics. Based on the images obtained, it is possible to calculate characteristics of the RPE cell mosaics, such as the regularity of the mosaic (exhibited by the number of neighboring cells), cell density, photoreceptor density, cells spacing, nearest neighbor distance, and photoreceptor to RPE cell ratios. This information may be useful in determining the efficacy of therapies as well as the health of the eye.

Figure 26A:
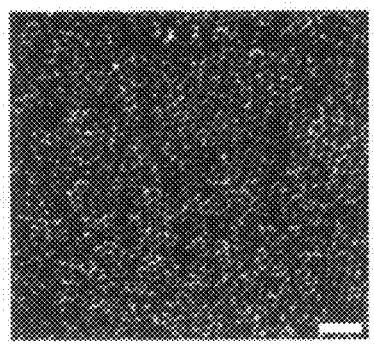
FIGS. 26(a)-26(d) illustrate exemplary primate RPE cells before and after Fourier Transform processing.
Figure 26B:
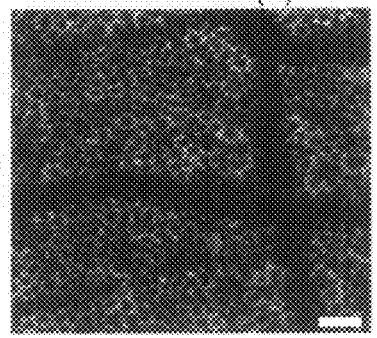
Figure 26C:
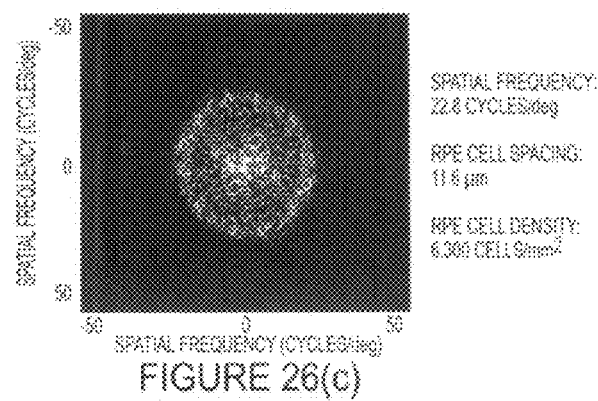
Figure 26D:
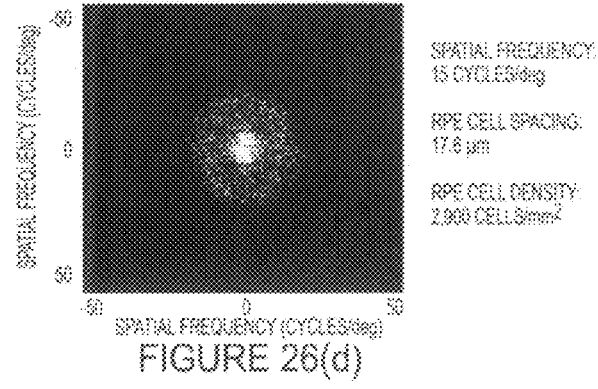

FIGS. 26(a)-26(d) illustrate spatial and frequency domain illustrations of RPE cells at the fovea and 10 degrees from the fovea. FIGS. 26(a) and 26(b) represent the RPE cell mosaics at those respective locations. FIGS. 26(c) and 26(d) illustrate the images of FIGS. 26(a) and 26(b) in the frequency domain.

Figure 27A:
FIGS. 27(a) and 27(b) illustrate the results of alternative registration methods.
Figure 27B:
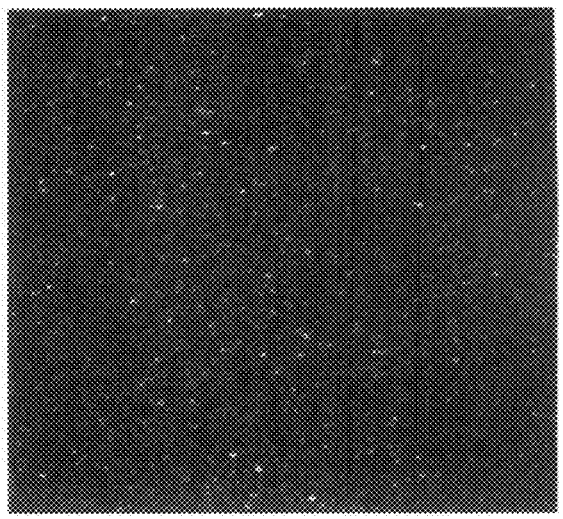

FIGS. 27(a) and 27(b) illustrate alternative registration methods. The data used to obtain FIGS. 27(a) and 27(b) is the same as the data used to obtain FIG. 5(b). The image in FIG. 27(a) was obtained by summing 1000 fluorescence frames. The image in FIG. 27(b) was obtained by summing 1000 fluorescence frames that were cross correlated and averaged. However, because the fluorescence images were not correlated using data obtained from a more detailed reflectance image (e.g., an image that has more photons), the final fluorescence images illustrated in FIGS. 27(a) and 27(b) are not as desirable as the images obtained according to the methods of the present invention.

Figure 28:
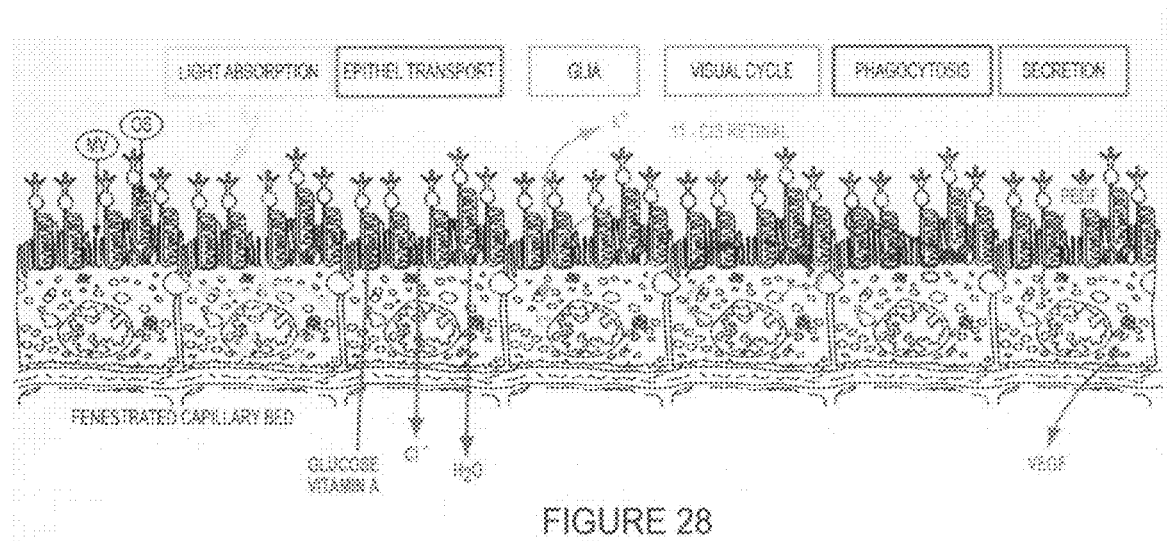
FIG. 28 illustrates exemplary functions of the retinal pigment epithelium.

FIG. 28 illustrates function of the retinal pigment epithelium. These functions include light absorption, epithet transport, glia, visual cycle, phagocytosis, and secretion.

The exemplary retrograde labeling method described above may be advantageous in situations where it is desirable to image cells repeatedly. In this non-limiting example, it was possible to observe cell labeling for at least five months in vivo. This may be very useful, for example, for retinal disease experiments such as imaging the same ganglion cells before, during, and after glaucoma occurs. Additionally, fully functional ganglion cell types may be distinguished in vivo by techniques such as selective dye injections into different regions, such as different regions of the LGN. Combining these techniques with creating a lesion to inactivate a cell type, followed by behavioral testing of the living animal, would permit direct analysis of the perceptual role of ganglion cells, among other things.

Additionally, experimentation with the photodynamics of rhodamine dextran dye in the in vivo preparation may yield a variety of results. For example, when increasing light exposure, local brightening of the ganglion cell fluorescence may be observed, as shown in FIGS. 4(a)-4(d). This photodynamic effect may cause dendritic field arbors to become visible, such that it may be possible to classify individual cells based on their dendritic morphology. See, e.g., D. M. Dacey et al., *Fireworks in the Primate Retina: in Vitro Photodynamics Reveals Diverse LGN-Projecting Ganglion Cell Types*, Neuron 37, 15-27 (2003), the contents of which are herein incorporated by reference. As a result, it is possible to photo-fill selected ganglion cells where the increased light caused the dye to release from the lysosomes in the cell and fill the entire cell, including its dendrites. This increased brightening phenomenon may result from reduced self quenching, in which the dye concentration decreases as it spreads throughout the cell and into its dendrites. Combining the high resolution afforded by adaptive optics with the photo-filling properties of rhodamine dextran dye may be a way to image dendritic tree fields, providing a method to classifying ganglion cells morphologically in vivo as well as to improve the visualization of ganglion cell axons.

Combining confocal detection and high resolution adaptive optics in vivo for imaging creates a confocal fluorescence microscope for the eye, which permits experiments in the living eye that could otherwise only have been conducted in excised tissue. The ability to image a variety of microscopic retinal structures in the living eye may be especially useful in combination with physiological and/or psychophysical measurements. In vivo imaging enables the study of changes in normal and diseased retinas to be studied over extended periods of time (e.g., months or years) in a single animal, obviating the need to sacrifice multiple subjects at different time points for in vitro microscopic analysis. When applied to the study of retinal disease, these methods may enable earlier detection of disease and may facilitate development of effective therapies.

The combination of confocal detection, fluorescence imaging, adaptive optics, and multi-spectral imaging may be used to obtain high resolution in vivo images of retinal ganglion cells, retinal pigment epithelial cells, and the finest capillaries around the foveal avascular zone. These techniques may provide new information about ganglion cell and RPE cell morphology in normal and diseased retinas in vivo. When combined with psychophysical testing, this technique may also yield a new understanding of ganglion cell function. Additionally, the present invention need not be limited to the imaging of single cells, and may find applicability in imaging blood vessels and macroscopic features of the retina as well.

Another non-limiting aspect of the present invention provides for determining the presence, if any, of a disease in the subject's imaged tissue. This determination may be performed by analyzing the imaged tissue to identify any changes in the features therein that may occur over time. See, e.g., Baraas et al., *Adaptive Optics Retinal Imaging Reveals S-Cone Dystrophy in Tritan Color-Vision Deficiency*, 24 JOSA A, Issue 5, 1438-1447 (May 2007), the contents of which are incorporated herein by reference. Once a determination has been made of the presence, absence, or progression of a disease, treatments may be adjusted accordingly. In other words, the present invention provides a method by which treatment efficacy may be monitored in vivo.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A method for in vivo imaging a retinal cell, the method comprising:
   obtaining a first, in-vivo image of the at least one retinal cell;
   obtaining a second, in-vivo image of the at least one retinal cell;
   adjusting at least one of the first, in-vivo image and the second, in-vivo image to account for a movement of the at least one retinal cell; and
   generating a final, in-vivo image based at least in part on the adjusting.

2. The method of claim 1, further comprising obtaining the first image and the second image simultaneously or substantially simultaneously.

3. The method of claim 1, wherein the first image is captured with a first detector and the second image is captured with a second detector.

4. The method of claim 1, wherein the first image is captured at a first frequency and the second image is captured at a second frequency.

5. The method of claim 1, wherein the generating step further comprises averaging the first image and the second image.

6. The method of claim 1, further comprising:
   providing at least one dye to the at least one cell; and
   optically exciting the at least one dye.

7. The method of claim 6, wherein the at least one dye includes at least one of rhodamine, Alexa 594, green fluorescence protein, and fluorescein.

8. The method of claim 6, wherein the providing includes injecting the at least one dye into at least one layer of a lateral geniculate nucleus (LGN).

9. The method of claim 1, wherein the cell includes at least one of a retinal ganglion, a retinal pigment epithelial cell, a capillary cell, and a Muller cell.

10. The method of claim 6, wherein the exciting includes exciting the at least one dye using at least one of a 530 nm light, a 568 nm light, 830 nm light, and a 904 nm light.

11. The method according to claim 6, wherein the obtaining includes obtaining the at least one image using an adaptive optics scanning laser ophthalmoscope (AOSLO).

12. The method according to claim 11, wherein the AOSLO includes at least two imaging lasers and at least two detectors.

13. The method according to claim 6, wherein the obtaining includes obtaining at least two images from at least two spectral bands simultaneously or approximately simultaneously.

14. The method of claim 1, wherein the first image includes at least one of a reflectance image and a fluorescence image.

15. The method of claim 14, wherein the second image includes at least one of a reflectance image and a fluorescence image.

16. The method of claim 1, wherein the second image includes at least one of a reflectance image and a fluorescence image.

17. The method of claim 1, further comprising:
obtaining a reflectance image of the at least one cell;
obtaining a fluorescence image of the at least one cell;
adjusting at least one of the reflectance image and the fluorescence image to account for a movement of the at least one cell; and
generating the final, in-vivo image based at least in part on the adjusting.

18. The method of claim 17, further comprising removing warp from at least one of the at least two images.

19. The method of claim 18, wherein the removing includes:
measuring horizontal warp using a linear line-pair grating positioned at a focal plane of a model eye lens inserted at a pupil plane of the eye; and
performing at least one of stretching and compressing the at least one of the at least two images to correct the warp.

20. The method of claim 17, wherein the at least one cell includes at least one blood vessel.

* * * * *